United States Patent
Smith et al.

(10) Patent No.: US 12,090,086 B2
(45) Date of Patent: Sep. 17, 2024

(54) METHODS AND SYSTEMS FOR DISSIPATING THERMAL LOADS IN WEARABLE DEVICES

(71) Applicant: EMBR Labs IP LLC, Boston, MA (US)

(72) Inventors: Matthew J. Smith, Somerville, MA (US); Kristen Warren, Cambridge, MA (US); James Edwin Pendergrast, Somerville, MA (US)

(73) Assignee: EMBR Labs IP LLC, Boston, MA (US)

( * ) Notice: Subject to any disclaimer, the term of this patent is extended or adjusted under 35 U.S.C. 154(b) by 1056 days.

(21) Appl. No.: 16/962,322

(22) PCT Filed: Jan. 11, 2019

(86) PCT No.: PCT/US2019/013348
§ 371 (c)(1),
(2) Date: Jul. 15, 2020

(87) PCT Pub. No.: WO2019/152172
PCT Pub. Date: Aug. 8, 2019

(65) Prior Publication Data
US 2020/0352777 A1   Nov. 12, 2020
US 2021/0315731 A9   Oct. 14, 2021

Related U.S. Application Data

(60) Provisional application No. 62/624,465, filed on Jan. 31, 2018.

(51) Int. Cl.
*A61F 7/00*   (2006.01)
*A61B 5/01*   (2006.01)
(Continued)

(52) U.S. Cl.
CPC ............ *A61F 7/00* (2013.01); *A61B 5/01* (2013.01); *F28F 27/00* (2013.01); *G06F 1/163* (2013.01);
(Continued)

(58) Field of Classification Search
CPC ............ A61F 7/00; A61F 2007/0093; A61F 2007/0095; A61F 7/007; A61F 2007/0075;
(Continued)

(56) References Cited

U.S. PATENT DOCUMENTS 8,397,518 B1   3/2013   Vistakula
10,182,937 B2   1/2019   Smith et al.
(Continued)

FOREIGN PATENT DOCUMENTS

JP   H09-154867 A      6/1997
JP   2014028130 A  *   2/2014   .............. A61F 7/00
JP   2016-538972 A    12/2016

OTHER PUBLICATIONS

U.S. Appl. No. 16/214,372, filed Dec. 10, 2018, Smith et al.
(Continued)

*Primary Examiner* — Sean W Collins
(74) *Attorney, Agent, or Firm* — Wolf, Greenfield & Sacks, P.C.

(57) ABSTRACT

Systems and methods for manipulating the temperature of a surface are described. Described embodiments include thermal adjustment devices that may include a heatsink and that are operated in two or more modes of operation to apply a desired temperature to a user. In one operating mode the thermal adjustment device may apply a first temperature to an underlying surface while generating heat at a rate faster than the heatsink's heat dissipation rate. The thermal adjustment device may then apply a second temperature to reduce
(Continued)

the rate of heat generation to be less than the heatsink's heat dissipation rate. These modes of operation may be applied cyclically to permit continuous operation of the thermal adjustment device. In some embodiments, the temperature profile applied when changing between the modes of operation may be selected such that the user experiences either a reduced, or substantially, neutral thermal sensation.

51 Claims, 11 Drawing Sheets

(51) Int. Cl.
  *F28F 27/00* (2006.01)
  *G06F 1/16* (2006.01)
  *H01L 23/38* (2006.01)

(52) U.S. Cl.
  CPC ............ *A61F 2007/0075* (2013.01); *A61F 2007/0086* (2013.01); *A61F 2007/0093* (2013.01); *A61F 2007/0095* (2013.01); *H01L 23/38* (2013.01)

(58) Field of Classification Search
  CPC . A61B 5/01; F28F 27/00; G06F 1/163; H01L 23/38
  See application file for complete search history.

(56) References Cited

U.S. PATENT DOCUMENTS

| | | |
|---|---|---|
| 2007/0193278 A1 | 8/2007 | Polacek et al. |
| 2015/0101788 A1* | 4/2015 | Smith ............... A61F 7/007 62/3.5 |
| 2017/0242463 A1* | 8/2017 | Matteson ............... G05B 15/02 |
| 2018/0042761 A1 | 2/2018 | Smith et al. |
| 2019/0110950 A1 | 4/2019 | Smith et al. |

OTHER PUBLICATIONS

U.S. Appl. No. 16/891,821, filed Jun. 3, 2020, Smith et al.
U.S. Appl. No. 15/555,677, filed Sep. 5, 2017, Smith et al.
U.S. Appl. No. 16/891,781, filed Jun. 3, 2020, Smith et al.
U.S. Appl. No. 16/344,577, filed Apr. 24, 2019, Smith et al.
U.S. Appl. No. 17/109,749, filed Dec. 2, 2020, Smith et al.
U.S. Appl. No. 16/129,182, filed Sep. 12, 2018, Smith et al.
U.S. Appl. No. 17/109,790, filed Dec. 2, 2020, Smith et al.
PCT/US2019/013348, Apr. 11, 2019, International Search Report and Written Opinion.
International Search Report and Written Opinion for International Application No. PCT/US2019/013348 mailed Apr. 11, 2019 (W1034. 70005WO00).

* cited by examiner

METHODS AND SYSTEMS FOR DISSIPATING THERMAL LOADS IN WEARABLE DEVICES

CROSS-REFERENCE TO RELATED APPLICATIONS

This application is a National Stage filing under 35 U.S.C. § 371 of international application serial number PCT/US2019/013348, filed on Jan. 11, 2019, which claims the benefit of priority under 35 U.S.C. § 119(e) of U.S. provisional application Ser. No. 62/624,465, filed Jan. 31, 2018, the disclosures of each of which are incorporated by reference in their entirety.

FIELD

Disclosed embodiments are related to methods and systems for dissipating thermal loads in wearable devices.

BACKGROUND

Thermoelectric cooling systems have been of great interest for applying cooling to the human body. Also, improving battery capacity has made it possible to integrate electronic devices into wearable technology. Applications for these types of thermoelectric systems for cooling the human body include migraine relief, wrinkle control, thermal relief from menopausal hot flashes, providing personal comfort within buildings, improving human performance in extreme environments, and other appropriate applications. Thermoelectrics offer several advantages in such applications including low form factors (especially compared with compressor technology), no moving parts which may be mechanically robust and silent, and precise dynamic control over temperature profiles applied by the device. To handle the thermal loads generated by the use of these thermoelectric systems, prior systems have used heat management solutions such as evaporative cooling, forced convection using a combination of heatsinks and fans, and terminating device operation after a set duration and/or after a preset temperature is reached.

SUMMARY

In one embodiment, a device for manipulating a temperature of a surface includes at least one heating and/or cooling element constructed and arranged to be disposed adjacent the surface and a heatsink in thermal communication with the at least one heating and/or cooling element and an external environment of the device. The device also includes a controller in electrical communication with the at least one heating and/or cooling element. The controller is configured to cause the at least one heating and/or cooling element to apply a first operating temperature to the surface with a first temperature profile during a first operating mode, and the controller is configured to cause the at least one heating and/or cooling element to apply a second temperature to the surface with a second temperature profile during a second operating mode. The second temperature is between the first operating temperature and a temperature of the heatsink, and the heatsink dissipates a thermal load while the second temperature is applied to the surface.

In another embodiment, a method for manipulating a temperature of a surface includes: applying a first temperature to the surface with a first temperature profile; applying a second temperature to the surface with a second temperature profile; and dissipating heat from a heatsink while the second temperature is applied to the surface, wherein the second temperature is between the first temperature and a temperature of the heatsink.

In yet another embodiment, a method for manipulating a temperature of a surface includes: cyclically applying at least first and second modes of operation to apply thermal stimulation to the surface. The first operating mode includes applying a first temperature to the surface with a first temperature profile while generating heat at a first rate of heat generation and dissipating heat with a heatsink with a first rate of heat dissipation. The first rate of heat dissipation is less than the first rate of heat generation. The second operating mode includes applying a second temperature to the surface with a second temperature profile while generating heat at a second rate of heat generation and dissipating heat with the heatsink with a second rate of heat dissipation. The second rate of heat dissipation is greater than the second rate of heat generation.

In still another embodiment, a device for manipulating a temperature of a surface includes at least one heating and/or cooling element constructed and arranged to be disposed adjacent the surface, and a heatsink in thermal communication with the at least one heating and/or cooling element and an external environment of the device. The device also includes a controller in electrical communication with the at least one heating and/or cooling element. The controller is configured to cause the at least one heating and/or cooling element to cyclically apply at least first and second modes of operation to apply thermal stimulation to the surface. During the first operating mode the controller is configured to cause the at least one heating and/or cooling element to apply a first temperature to the surface with a first temperature profile while generating heat at a first rate of heat generation and dissipating heat with the heatsink with a first rate of heat dissipation. The first rate of heat dissipation is less than the first rate of heat generation. During the second operating mode the controller is configured to cause the at least ogre heating and/or cooling element to apply a second temperature to the surface with a second temperature profile while generating heat at a second rate of generation and dissipating heat with the heatsink with a second rate of dissipation. The second rate of dissipation is greater than the second rate of generation.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
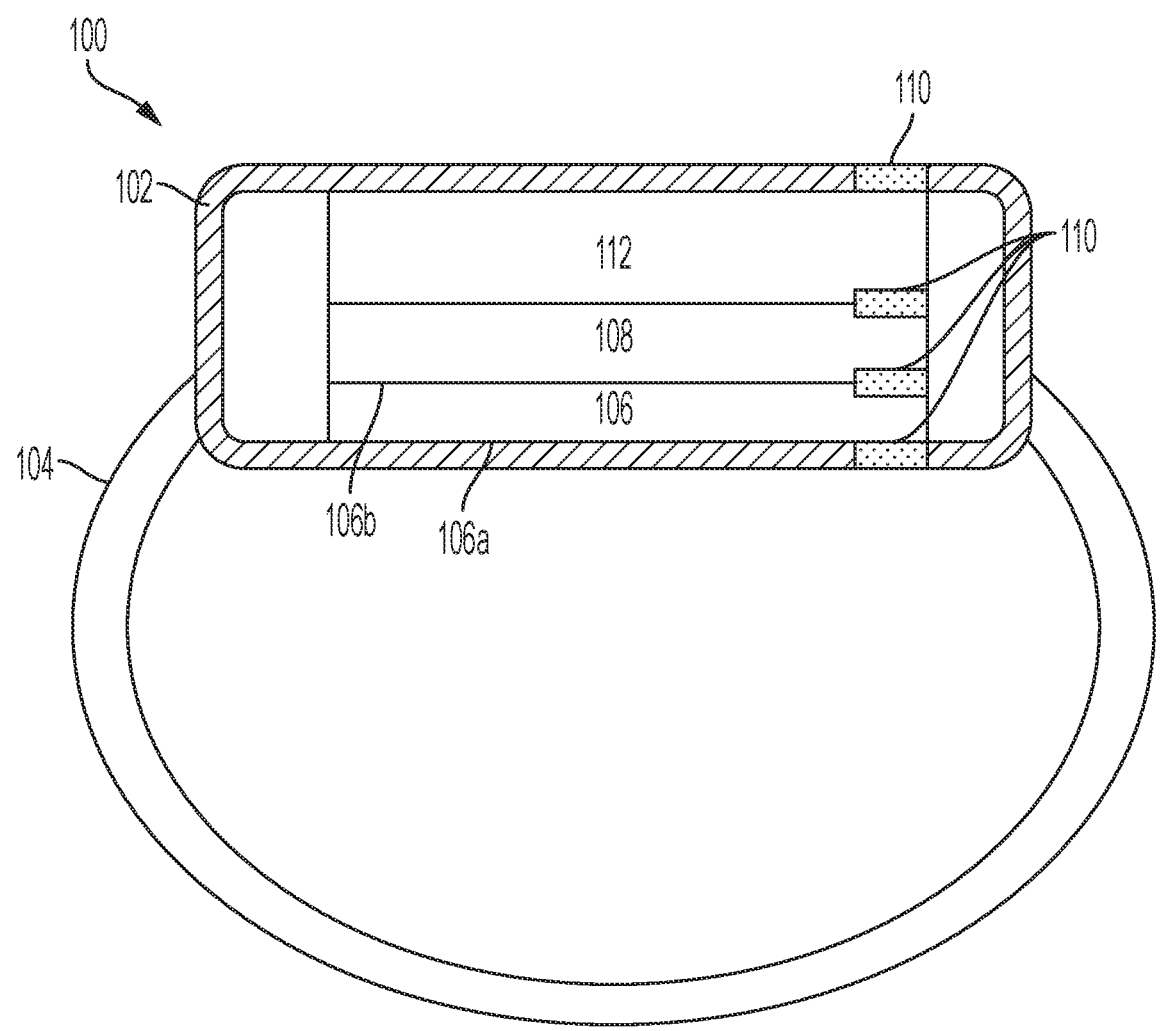
FIG. 1 is a schematic representation of one embodiment of a thermal adjustment device.

The Inventors have recognized that the use of either limited duration, bulky, and/or large power consumption cooling strategies have limited the use of thermal adjustment devices for various applications. Additionally, as outlined further below, the Inventors have recognized that prior systems that operate by simply turning off after a predetermined operating duration and/or a predetermined temperature has been reached may result in an undesired thermal sensation being applied to a user. Specifically, as an associated heatsink equilibrates to the surrounding environmental temperature, elevated temperatures are applied to the user. Accordingly, the Inventors have recognized that it may be desirable to operate a thermal adjustment device, which may be wearable in some applications, in a manner that permits heat from an associated heatsink to be dissipated to the surrounding environment without generating undesired thermal sensations for a user. For example, it may be undesirable to apply a warming thermal sensation to a user that is using the thermal adjustment device to provide a cooling thermal sensation. Thus, since the undesired thermal sensations are avoided, such a process may enable the thermal adjustment device to be continuously worn and remain in contact with the skin of a user through any number of alternating cycles of applying a desired thermal sensation to the user and thermal dissipation.

Based on the forgoing, the Inventors have recognized the benefits associated with a thermal adjustment device including a heatsink used for storing and dissipating thermal energy from the system. However, such a system may present several competing factors when designing a system to operate continuously. For example, when the thermal adjustment device includes one or more thermoelectric materials, there are competing mechanisms between the dissipation of heat from the passive heatsink and the generation of heat within the thermoelectric material. Specifically, the more heat the heatsink stores, i.e. the higher the temperature of the heatsink, the better the heatsink is at dissipating heat into the environment, i.e. faster heat dissipation rates. However, higher temperatures reduce the efficiency of the thermoelectric, thus, the thermoelectric generates more waste heat at higher temperatures that is either stored or dissipated by the heatsink to generate the same amount of cooling.

FIG. In view of the above, the inventors have recognized the benefits associated with operating a thermal adjustment device in a manner that balances heat generated within the device and heat that is dissipated into the environment during continuous operation of the thermal adjustment device during two or more modes of operation. For example, in one embodiment, in a first operating mode, a thermal adjustment device may apply a first operating temperature to a surface, such as the skin of a user, for a first duration during which an associated heatsink of the device may increase in temperature. In a second operating mode, the thermal adjustment device may then apply a second temperature to the surface for a second duration. The thermal adjustment device may dissipate heat from the heatsink of the thermal adjustment device while the second temperature is applied to the surface. In some embodiments, the second temperature may be between the first temperature and a temperature of the heatsink. By maintaining a temperature of the surface at a desired temperature during heat dissipation from the heatsink, it may be possible to prevent the application of undesired thermal sensations to a user during thermal equilibration of the heatsink. After a desired duration, dissipating sufficient heat, and/or reaching an appropriate heatsink temperature, the thermal adjustment device may return to normal operation to apply a desired thermal sensation to a user including, for example, returning to the first temperature.

It should be understood that the heatsinks discussed above and elsewhere in the current disclosure may refer to either a passive and/or an active heatsink. Specifically, a passive heatsink may correspond to a thermally conductive material (heatsink) that dissipates heat into the environment through a combination of natural convection, radiative cooling, and convection due to movement of the device if worn without the aid of a fan or other active component. This is in contrast to an active heatsink where forced convection is used to remove heat from a heatsink using either a fan or pump to blow a fluid over or through the heatsink as well as heatsinks where evaporative cooling is implemented. However, a passive heatsink may offer significant advantages when incorporated in a wearable or portable application. For example, a passive heatsink may be designed to have a low form factor and the passive heatsink has no moving parts which may increase a reliability of the overall system. However, passive heatsinks are relatively poor at dissipating heat. Accordingly, prior systems that utilized passive heatsinks were designed to be removed from the body after a period of use to allow the heatsink to cool down. In contrast, the currently described systems may be used continuously through the use of two or more alternating modes of operation even when a passive heatsink is used to dissipate the thermal energy generated during use. Additionally, in some embodiments, a smaller actively cooled heatsink that would not otherwise be capable of cooling a thermal adjustment device sufficiently for continuous operation may also be enabled through the use of the disclosed operating methods. Accordingly, it should be understood that the currently disclosed thermal adjustment devices and methods of operation are not limited to any particular type of heatsink as the disclosure is not so limited.

It should be understood that the above noted second temperature applied to a surface during heat dissipation from a heatsink may correspond to any appropriate temperature that permits a temperature of the heatsink to return to a desired operating temperature. However, in one embodiment, the second temperature may be between an initial temperature of the surface, i.e. initial skin temperature, and a temperature of the heatsink. Alternatively, in another embodiment, the second temperature may be between the initial temperature of the surface and the first temperature applied to the user during normal operation. Additionally, while a constant second temperature may be applied, in some embodiments, the second temperature applied to a surface during heatsink equilibration may be a variable temperature as the disclosure is not so limited. Specific considerations related to these different operating regimes are elaborated on further below.

It should be understood that the temperatures applied during the various modes of operation, i.e. during normal operation and during heat dissipation, may either be the same and/or different during subsequent cycles of a thermal adjustment device during continuous operation. For example, in one embodiment, a thermal adjustment device may apply the same temperature profile during subsequent normal and heat dissipation modes of operation. Alternatively, the temperature profiles and/or absolute temperatures applied during the different modes of operation may be varied between subsequent normal and heat dissipation modes of operation. Additionally, as elaborated on below, the temperatures applied to a user may vary and/or be constant during individual portions of a cycle of the thermal adjustment device and/or the applied temperature may vary. Thus, the first and second temperatures described herein may be understood to correspond to first and second temperature profiles that are applied during the different modes of operation. Additionally, the currently disclosed modes of operation may correspond to any number of different types of temperature profiles and/or temperatures as the disclosure is not limited in this fashion.

While the currently disclosed systems and methods may be used for any appropriate application, the above embodiment enables the operation of a wearable thermal adjustment system, such as a thermoelectric cooling system, in the manner described herein. Further, such a system overcomes the shortcomings of prior systems that included passive heatsinks by using the heatsink as a heat storage device during an active cooling mode which may be followed by discharging of the stored heat into the environment without generating undesired thermal sensations for the user. Additionally, such a system provides advantages compared to actively cooled systems with reduced bulk and power consumption. However, while certain advantages are noted above, it should be understood that depending on the particular embodiment, a system may exhibit either some and/or different advantages than those noted above as the disclosure is not limited in this fashion.

A transition between a normal operating mode of a thermal adjustment device, such as an active cooling mode where cooling temperatures are applied to a user, and a thermal dissipation mode of the thermal adjustment device may be implemented in any appropriate fashion. For example, in one embodiment, a transition between these operating modes may be initiated upon the detection of one or more operating parameters of the thermal adjustment device exceeding one or more corresponding thresholds. In some embodiments, the thermal adjustment device may transition back to a normal operating mode after the one or more operating parameters has dropped back below either the initial threshold and or a second lower threshold which would correspond to a hysteresis threshold reset. Appropriate operating parameters that may be monitored include, but are not limited to, a temperature of a heating and/or cooling element, a temperature differential across a heating and/or cooling element (e.g. a temperature differential between the opposing sides of a thermoelectric module), a temperature of the heatsink and/or housing (e.g. in some embodiments a portion of the housing may correspond to the heatsink), heat flux between the heatsink and the corresponding cooling and/or heating element, power consumption of a heating and/or cooling element to maintain a desired temperature, and/or any other appropriate parameter. In one exemplary embodiment, the thermal adjustment device may transition from normal operation mode to a thermal dissipation mode when a temperature of the heatsink exceeds a threshold temperature. The thermal adjustment device may then transition back to normal operation mode when the detected heatsink temperature is subsequently reduced to a temperature less than either the initial threshold temperature or a second lower threshold temperature depending on the embodiment.

The various operating parameters rioted herein may be measured using any appropriate technique. For example, temperatures of the various components may be monitored using any appropriate temperature probe including thermocouples and thermistors. Heat flux to and/or from the heatsink may be measured directly using a heat flux sensor; indirectly using techniques such as a temperature difference across a thermoelectric material to infer the heat flux, and/or using any other appropriate method. Power consumption of the heating and/or cooling elements may be monitored using any appropriate power, voltage, and/or current monitoring arrangement capable of detecting a power applied to the heating and/or cooling elements. Thus, it should be understood that the current disclosure is not limited to any specific method of monitoring the parameters discussed herein.

In some embodiments, it may be desirable to control a thermal sensation applied to a user during dissipation of a thermal load that has been applied to a heatsink. For example, after applying a cooling thermal sensation to a user, it may be undesirable to apply a warm sensation to the same user. Accordingly, in some embodiments, it may be desirable to avoid simply turning off a thermal adjustment device which would permit the entire system to equilibrate to a temperature between the two extremes of the heatsink and the corresponding one or more heating and/or cooling elements. Instead, in some embodiments, the temperature applied to the underlying surface, i.e. the user's skin, may be changed to provide either a reduced or neutral thermal sensation during heat dissipation. Accordingly, the disclosed systems and methods enable a heatsink to be thermally discharged, i.e. cooled or warmed to a desired operating temperature without generating unwanted thermal sensations. Similar to the above, after the desired amount of thermal dissipation of the heatsink has been achieved the system may either return to normal operation for another operation cycle and/or the system may be shut down.

As elaborated on further below, a person's perception of temperature is a complex interaction of both absolute temperature, temperature difference relative to current skin temperature, and a rate of change of the temperature applied to the person's skin. Accordingly, when applying a temperature profile to a user that is intended to be "neutral", or to apply a reduced thermal sensation, the applied temperature profile may include temperatures and rates of temperature change as detailed below. In one embodiment, the temperature may be greater than or equal to 20° C., 25° C., 30° C., 31° C., 35° C. and/or any other appropriate temperature. Correspondingly, the applied temperature may be less than or equal to 40° C., 36° C., 35° C., 33° C., and/or any other appropriate temperature. Combinations of the above noted ranges are contemplated including, for example, temperatures applied to a user that are between or equal to 20° C. and 40° C., 30° C. and 36° C., 31° C. and 35° C. with a temperature of 36° C. being preferable in some embodiments, and/or any other appropriate range. These temperature ranges may be combined with rates of temperature change applied to a user's skin that are greater than or equal to 0.01° C./s (Celsius per second), 0.1° C./s, 0.2° C./s, and/or any other appropriate rate of temperature change. Applied rates of temperature change may also be less than or equal to 1.0° C./s, 0.5° C./s, 0.4° C./s, 0.3° C./s, and/or any other appropriate rate of temperature change. Combinations of these rates of temperature change are contemplated including, for example, a rate of temperature change between or equal to 0.01° C./s and 1.0° C./s, 0.01° C./s and 0.5° C./s, 0.1° C./s and 0.3° C./s, as well as 0.01° C./s and 0.1° C./s with a rate of temperature change of about 0.2° C./s being preferable in some embodiments. For example, in one specific embodiment, after applying a cooling temperature profile to a user, a thermal adjustment device may increase a temperature of an underlying adjacent surface, i.e. the user's skin, to 36° C. at a rate of 0.2° C./s to permit an associated heatsink to cool down while avoiding generating a perceived warming thermal sensation for the user. Of course, while a specific example is given, different combinations of the above described temperature ranges and rates are also contemplated as the disclosure is not so limited.

The above noted rates of temperature change, as well as other rates of temperature change described herein, may either refer to an average rate of temperature change during a particular portion of a temperature profile when changing from a first temperature to a second temperature and/or they may refer to a temperature change rate that is applied during at least a portion of the applied temperature profile. For example, variable or constant temperature change rates may be applied when changing from a first temperature to a second temperature. Therefore, a particular rate may either be applied during at least a portion of the noted temperature change and/or the rate may correspond to an average rate during the noted temperature change.

It should be understood that the above noted temperatures used during a heat dissipation mode may be combined with any appropriate range of temperatures used to apply either a warming and/or cooling thermal sensation to a user during a normal operating mode. For example, temperatures between or equal to 15° C. and 45° C., 20° C. and 40° C., 20° C. and 27° C., 30° C. and 40° C., and/or any other appropriate temperature range may be used during a normal operating mode.

While a method of operating a device without creating unwanted thermal sensations is described above, embodiments in which a thermal adjustment device is operated in a manner that applies a warming sensation after cooling a user and/or a cooling sensation after warming a user are contemplated as the disclosure is not so limited.

In some embodiments, a thermal adjustment device may include one or more heating and/or cooling elements (e.g., thermoelectric materials) that may be positioned directly adjacent to the skin of a user. An electrical input, for example in the form of an electrical signal, may be applied to the heating and/or cooling element(s) by an associated controller so as to manipulate the temperature of the surface of the skin, for example, in the form of a temperature profile. As detailed further below, the applied temperature profile may either be a constant, varying, and/or alternating temperature profile. It should also be appreciated that any suitable heating and/or cooling element may be employed. For example, a heating and/or cooling element may correspond to a resistive heating device, convective thermal device, radiative thermal device, thermoelectric materials, or any other suitable apparatus that may be capable of generating a desired temperature profile to apply to a person's skin. In certain embodiments, thermoelectric materials may be preferred.

The term thermoelectric, thermoelectric material, thermoelectric module, and other similar terms are given their ordinary meaning in the art and refer to materials in which a temperature change is generated at a surface of the material upon application of an electric potential (e.g., voltage and corresponding current), in accordance with the thermoelectric effect (e.g., often referred to by other names such as the Peltier, Thomson, and Seebeck effects). Any suitable thermoelectric may be employed, a number of which are described further below. It should be understood that, while a portion of the description herein describes thermoelectric materials, the present disclosure is not limited to thermoelectric materials, and other thermal adjustment apparatuses may be employed where appropriate.

The term resistive heater is given its ordinary meaning in the art and refers to materials in which a temperature increase is generated at a surface of the material upon application of an electric potential (e.g., voltage and corresponding current), in accordance with joule heating. Any suitable resistive heating element may be employed, which could use any electrical conductor with sufficient resistance to generate joule heating. It should be understood that, while a portion of the description herein describes resistive heating elements, the present disclosure is not limited to resistive heating, and, other heating apparatuses may be employed where appropriate.

In some embodiments, not shown in the figures, the devices and systems disclosed herein may be incorporated into a wearable article (e.g., an article of clothing). For example, in certain embodiments, a thermal adjustment device as described herein may be incorporated in a scarf, necklace, armband, wristband, hat, shirt, vest, pants, leggings, sleeves, or any other suitable wearable article capable of being worn on any appropriate portion of a person's body. The size of the device may be selected, in some embodiments, such that the device fits comfortably on or around a wrist, an ankle, a head, a neck, a torso, an arm, a leg, a calf, and/or any other appropriate portion of a person's body. Additionally, in some embodiments, a thermal adjustment device may be sized such that it fits within an article of clothing, within the palm of a user's hand, or any other appropriate size. Additionally, embodiments in which a thermal adjustment device is not incorporated into a wearable article are also contemplated. For example, a thermal adjustment device may configured such that it may be applied manually by a person and/or may be incorporated into a separate stationary system. Accordingly, it should be understood that the currently disclosed devices and systems are not limited to any particular form factor and/or size.

For the sake of convenience the following embodiments and examples are primarily described relative to a thermal adjustment device that is used to apply a cooling sensation to a user. Accordingly, in these embodiments, the second modes of operation during heat dissipation correspond to an associated heatsink cooling down in temperature during a heat dissipation mode. However, embodiments in which a thermal adjustment device applies a warming sensation during a normal operating mode and increases a temperature of a corresponding heatsink during a thermal dissipation mode in which a temperature of the heatsink increases are also contemplated as the disclosure is not so limited.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 2A:
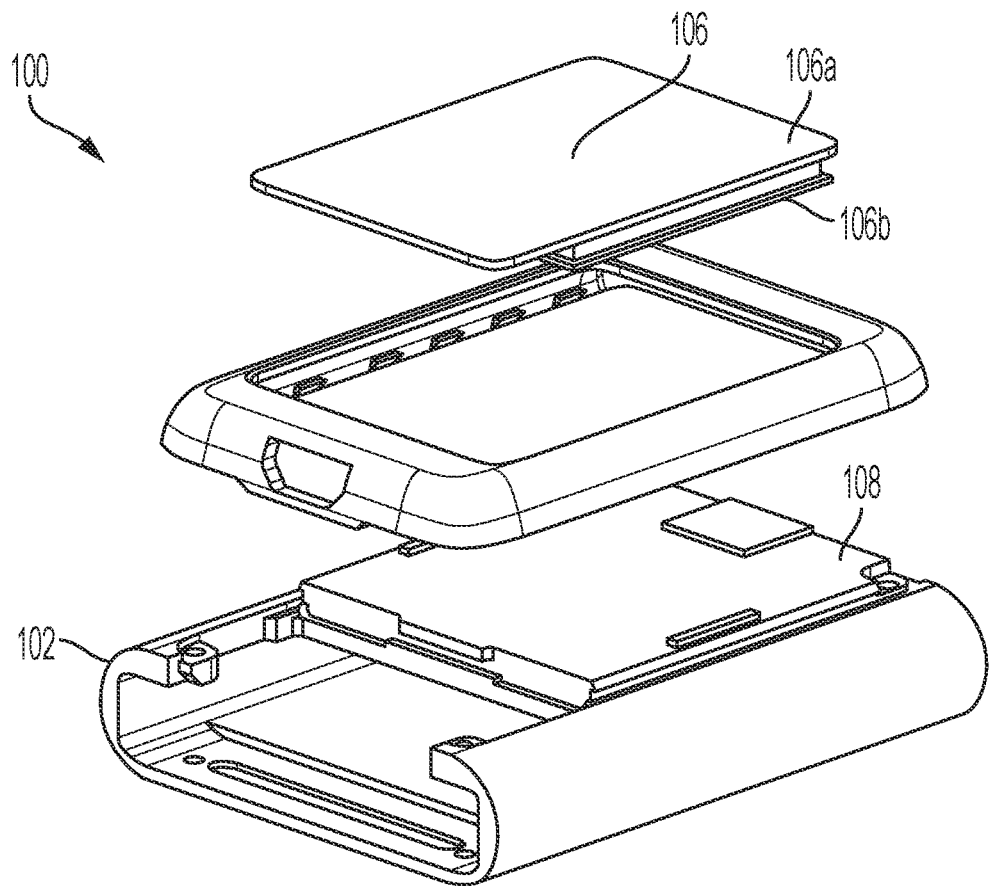
FIG. 2A is a schematic exploded perspective view of one embodiment of a thermal adjustment device without the battery depicted.
Figure 2B:
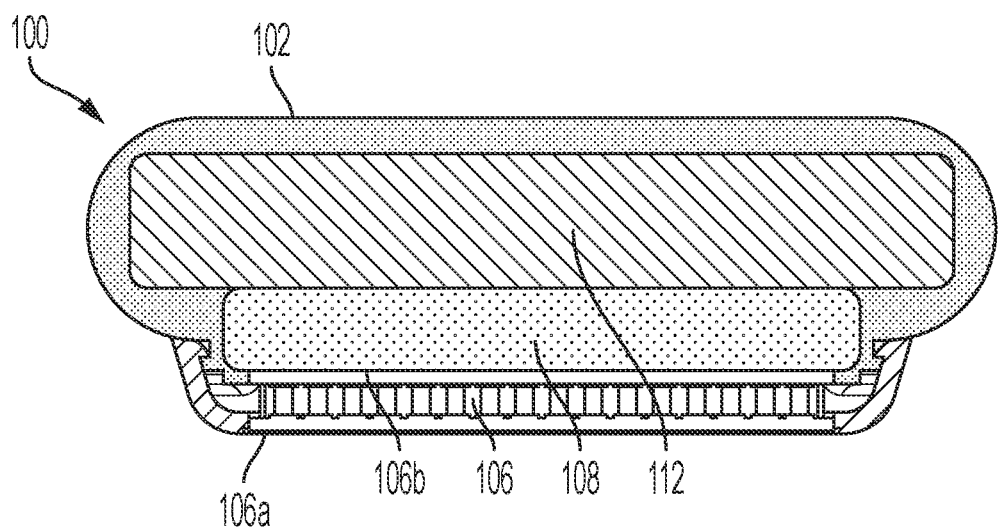
FIG. 2B is a cross sectional view of the embodiment of the thermal a device of FIG. 2B with the battery depicted.

FIGS. 1-2B depict embodiments of a thermal adjustment device 100 that may be used to provide thermal stimulation to a user. In some embodiments, the thermal adjustment device is in the form of a bracelet that is wearable on a wrist, ankle, leg, and/or arm of a user. However, as noted previously, the thermal adjustment device may be disposed adjacent to any appropriate portion of the user's body and may be integrated into any appropriate wearable article that may maintain the thermal adjustment device adjacent a desired location on the user's body. As depicted in the figures, the thermal adjustment device may include a housing 102 and a hand 104, or other appropriate structure, that is configured to maintain the thermal adjustment device adjacent to the desired portion of the user's body. Within the housing, the thermal adjustment device may include one or more heating and/or cooling elements 106 that may be configured to apply thermal stimulation to an associated part of a user's body that the thermal adjustment device is disposed adjacent to. The thermal adjustment device may include a controller 108 that is in electrical communication with the at least one heating and/or cooling element 106. Specifically, the controller may configured to cause the at least one heating and/or cooling element to apply one or more desired temperature profiles to a user during the various operating modes as detailed further below. The thermal adjustment device may also include one or more sensors 110 that are operatively coupled to the controller. The sensors may be configured to sense one or more operating states of the thermal adjustment device and/or one or more physical states of a user. Additionally, as depicted in the figures, the sensors may be disposed in any number of different positions within the device including, for example, on an exterior portion of the housing, a portion of the housing located adjacent a user's skin when worn, on opposing sides of the heating and/or cooling element, on the controller, and/or any other appropriate portion of the thermal adjustment device as the disclosure is not so limited. The thermal adjustment device may also include a battery 112 that is operatively coupled to the controller.

In the depicted embodiments, a first surface 106a of the one or more heating and/or cooling elements 106 may be positioned such that it contacts an underlying surface, such as a user's skin when worn. The heating and/or cooling elements, the controller 108, and the battery 112 may be disposed within the exterior housing 102 in any appropriate manner such that a second surface 106b of the one or more heating and/or cooling elements, such as the hot side of a thermoelectric module, may be in thermal communication with the exterior housing or other appropriate structure that may be used as a heatsink. Further, in some embodiments, at least a portion, and in some instances the entire, housing may be made from a thermally conductive material that is in thermal contact with the one or more heating and/or cooling elements either directly or indirectly through one or more intervening components. In such an embodiment, heat generated by the one or more heating and/or cooling elements may flow to the one or more thermally conductive portions of the housing which may act as a passive heatsink to dissipate the applied thermal load. Further, as detailed below, depending on the particular operating mode, the heatsink may either dissipate heat at a rate that is either greater than, less than, and/or equal to the amount of heat generated by the one or more heating and/or cooling elements during different modes of operation.

In the above embodiment, the flow of heat from the one or more heating and/or cooling elements may either flow directly from the heating and/or cooling elements to the housing and/or the heat may flow through one or more intermediate components. For example, in the depicted embodiment, heat may flow from the one or more heating and/or cooling elements through one or more components such as the controller, battery, and/or any other intermediate component to the housing where it may be dissipated to the exterior ambient environment. However, embodiments in which at least a portion of the heating and/or cooling elements are in direct thermal contact with the housing or other heatsink are also contemplated.

While the thermal adjustment device depicted in the above embodiment includes a band, it should be understood that the thermal adjustment device may be incorporated into any other appropriate type of wearable device, component, or garment as previously discussed. Additionally, while a particular arrangement of the various components such as the housing, one or more heating and/or cooling elements, controller, and battery have been depicted in the figures, it should be understood that other constructions are also contemplated as the disclosure is not so limited.

Figure 3:
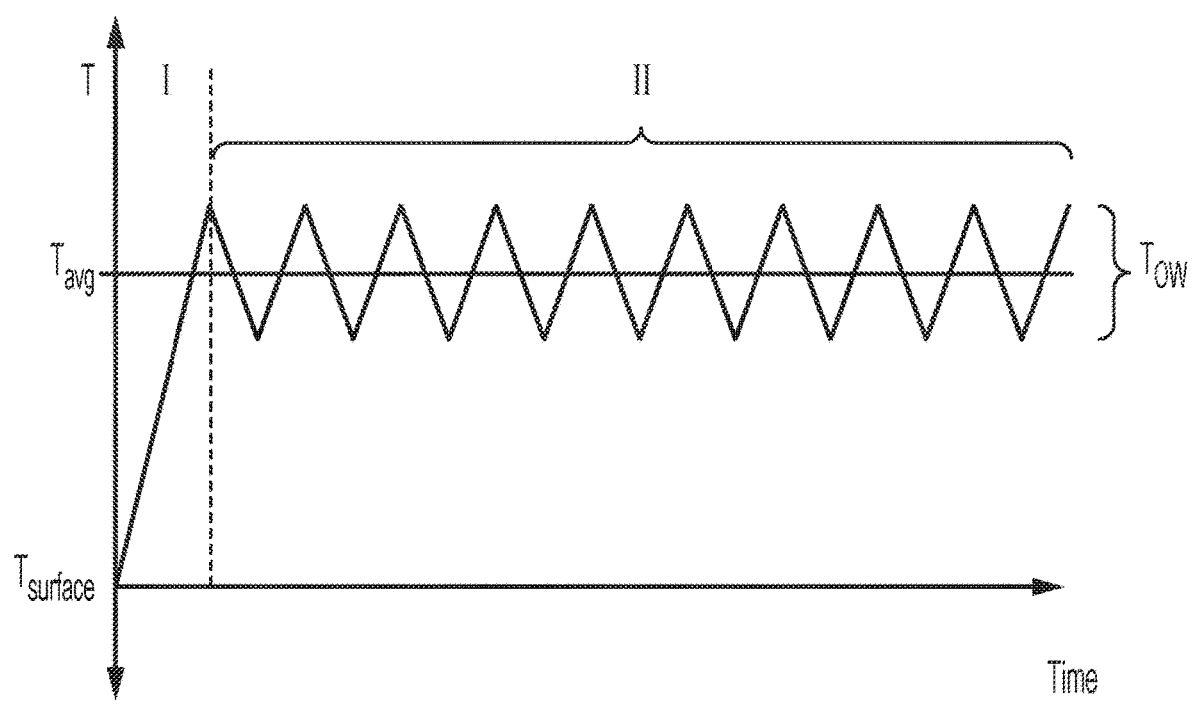
FIG. 3 is a graph of one embodiment of a temperature profile that may be applied using a thermal adjustment device.

The thermal adjustment devices described herein may be used to apply any number of different types of temperature profiles to a user including both cooling and/or warming sensations to a user. One specific embodiment of a temperature profile that may be applied to a corresponding portion of a user's body by a thermal adjustment device during a normal operating mode is depicted in FIG. 3. In the depicted graph, a temperature change relative to an initial temperature of a surface is plotted versus time. For the sake of clarity, the depicted embodiment illustrates temperatures that are greater than a corresponding temperature of the surface $T_{Surface}$ the thermal adjustment device is disposed against (i.e. the thermal adjustment device provides a warming sensation). However, the current disclosure is not limited in this fashion. For example, the thermal adjustment device may be operated to apply temperatures that are less than a corresponding initial temperature of the surface to provide a cooling sensation to a user. Additionally, embodiments in which both heating and/or cooling sensations are alternatingly applied with temperatures both greater than and less than the initial temperature of the surface are also contemplated.

As shown schematically in the figure, a temperature profile may have one or more portions including a ramp profile portion and/or one or more alternating temperature profile portions, i.e. one or a plurality of thermal pulses. For example, the temperature profile may comprise a first portion comprising a ramp profile portion (regime I) and a second portion comprising an alternating temperature profile portion (regime II) where the temperature of the thermal adjustment device cyclically varies between at least a first higher temperature and a second lower temperature. However, embodiments in which a constant temperature is applied during this portion of the temperature profile are also contemplated. In some embodiments, the alternating temperature profile portion may have an average frequency corresponding to the number of thermal pulses applied per unit time, $f_1$, an average temperature, $T_{avg}$, and an oscillation window, $T_{ow}$. The oscillation window is the difference between the maximum and minimum temperature for a given alternating temperature profile. The average temperature, $T_{avg}$, may be equal to a time average of the temperature, and thus may change depending on if the rates of increase and decrease of the temperature between the first higher temperature and the second lower temperature are different and/or if there are any constant temperature portions associated with the thermal pulses.

Again, while a particular temperature profile has been depicted in the figures and described above for one possible normal operating mode of a thermal adjustment device, the thermal adjustment devices described herein may be operated in any number of ways to apply any number of different types of temperature profiles to a user. Accordingly, the current disclosure should not be limited to any particular temperature profile for a given operating mode.

Figure 4:
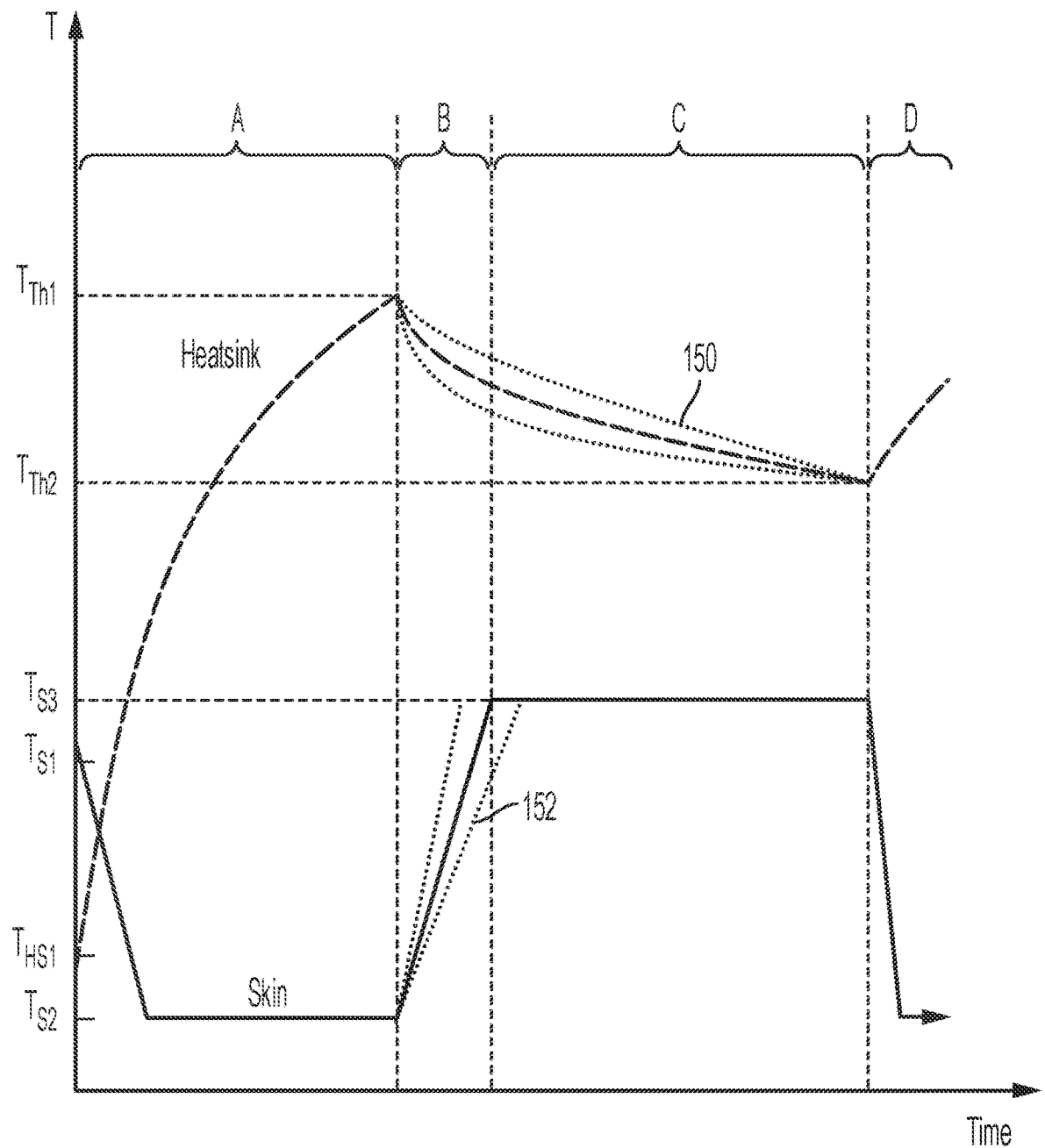
FIG. 4 is a graph of one embodiment of the corresponding temperature profiles of a heatsink and temperature applied to the skin of a user during operation of a thermal adjustment device.
Figure 5:
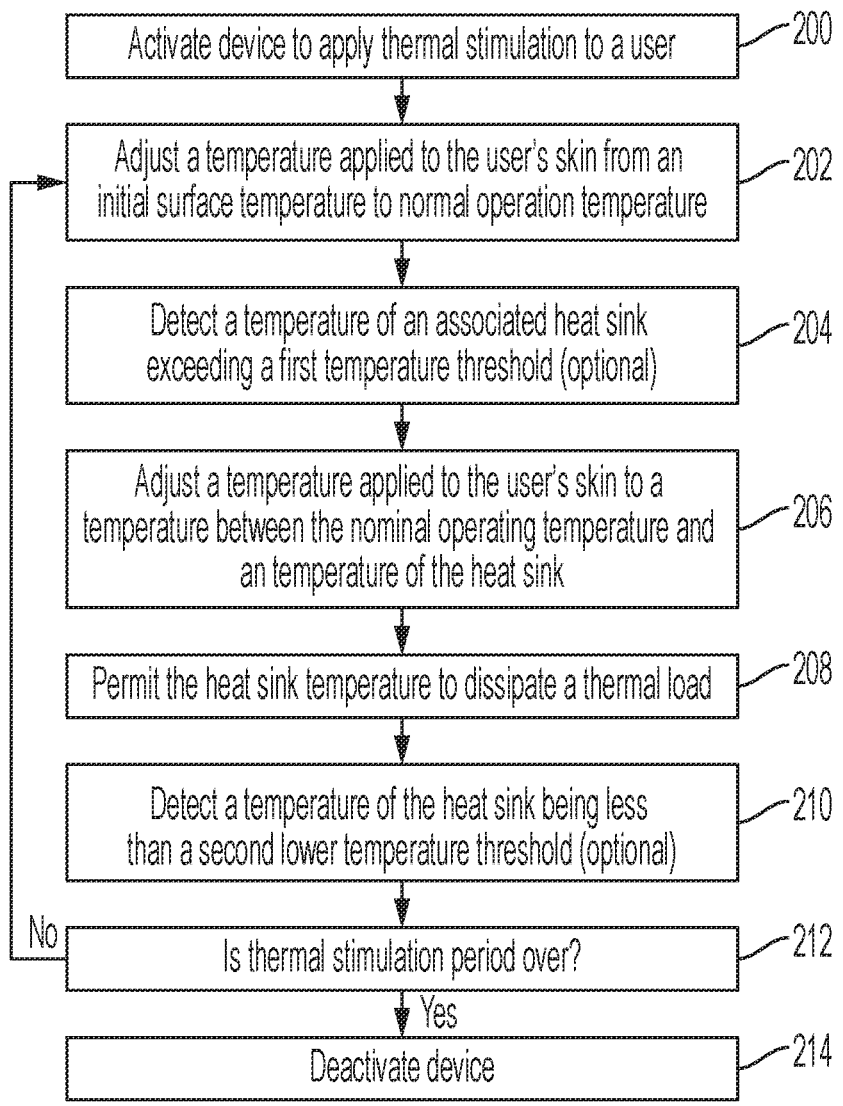
FIG. 5 is a flow diagram of one embodiment of a method for operating a thermal adjustment device to dissipate thermal loads of an associated heatsink.

As noted previously, in some applications it may be desirable to continuously operate a thermal adjustment device to deliver a magnitude of thermal stimulation, e.g. temperature change from initial skin temperature, that an associated heatsink, or other heat dissipation system, is unable to dissipate on a continuous basis. Accordingly, in some embodiments, and as shown in FIGS. 4 and 5, it may be desirable to operate a thermal adjustment device continuously using two or more modes of operation to maintain a balance of a thermal load generated during one or more modes of normal operation of the device and the amount of thermal load dissipated during one or more heat dissipation modes of operation. At 200 a thermal adjustment device may be activated to apply a desired thermal stimulation to an underlying surface such as a user's skin. Initially the skin, and a portion of the thermal adjustment device adjacent the skin, may be at an initial first surface temperature $T_{S1}$. An associated heatsink of the thermal adjustment device may also be at an initial first heatsink temperature $T_{HS1}$ which in some instances may correspond approximately to an ambient environmental temperature the heatsink is exposed to, which depending on the ambient environment may be greater than or less than the initial temperature of the surface. As shown in FIG. 4, during the initial ramping portion of period A, the thermal adjustment device changes the applied skin temperature to a second surface temperature $T_{S2}$, which in the depicted embodiment may be lower than the first surface temperature during step 202 of FIG. 5. Once a desired operating temperature is reached, the thermal adjustment device may finish the ramping portion of the applied thermal profile and apply a desired thermal sensation with a desired temperature profile for at least a first duration. The applied temperature profile may either be a constantly applied temperature and/or a varying temperature profile as the disclosure is not so limited. Of course, while the thermal adjustment device applies the desired thermal stimulation to a user, a corresponding temperature of the heatsink will correspondingly change, which in the depicted embodiment corresponds to an increasing heatsink temperature.

As shown by the transition between periods A and B in FIG. 4, the temperature of the associated heatsink may continue to increase until an operating parameter of the system, such as the depicted temperature of the heatsink reaches a first heatsink threshold temperature $T_{TH1}$, a time duration is exceeded, and/or another appropriate threshold is met. As noted previously, this threshold temperature condition may be determined using any appropriate detection technique including direct or indirect temperature measurements, heat flux measurements, and/or power measurements. Once it is detected that the desired operating parameter has exceeded the corresponding threshold at step 204, a controller of the thermal adjustment device may proceed to implementing a heat dissipation operating mode at steps 206 and 208 of FIG. 5.

As shown during period B of FIG. 4, the temperature applied to the skin by the thermal adjustment devices may be adjusted from the second surface temperature $T_{S2}$ to a third surface temperature $T_{S3}$ for at least a second duration as shown in Period C. As depicted in the figure, the third surface temperature may be between a temperature of the heatsink and the second surface temperature applied during normal operation of the device. Specifically, in the depicted embodiment, the third surface temperature may be between the initial first surface temperature and a temperature of the heatsink, such as the first heatsink threshold temperature, which may correspond to applying a neutral or warming thermal sensation to the user in some embodiments. However, in another embodiment, the third surface temperature may be between the initial first surface temperature and the second surface temperature which may correspond to applying a neutral or reduced cooling sensation to the user. In either case, and as detailed further below in regards to the examples, the third surface temperature may be selected such that the heatsink dissipates the applied thermal load at step 208 of FIG. 5 and as shown by the decreasing temperature of the heatsink in FIG. 4. Without wishing to be bound by theory, the heatsink is able to dissipate the thermal load because the one or more heating and/or cooling elements of the thermal adjustment device generate heat at a rate that is now less than rate at which the heatsink dissipates the generated heat during this second operating mode leading to the decreasing heatsink temperature observed during periods B and C. While a constant temperature profile has been illustrated in the figure during Period C, it should be understood that a variable temperature profile and/or thermal pulses may be applied to the surface as well.

At step 210 of FIG. 5, a controller of the thermal adjustment device may detect that an operating parameter of the device meets a second threshold. For example, a temperature of the heat sink may meet a second temperature threshold $T_{TH2}$. Thus, a second temperature threshold of the heatsink may be between the first larger temperature threshold $T_{TH1}$ and the third surface temperature $T_{S3}$ applied to the underlying surface during the heat dissipation mode, see FIG. 4. In some embodiments, the second temperature threshold be set such that it is larger than an expected ambient temperature the device will be operated in. Once the heatsink has cooled to the desired lower temperature, it may be determined whether or not a desired thermal stimulation period is over at step 212 of FIG. 5. If it is determined that the device operation is over, the device may be deactivated at 214. Alternatively, if device operation is intended to continue, a controller of the thermal adjustment device may return to normal operation where it may apply a desired temperature profile to the underlying surface. For example, as shown in period D of FIG. 4, the controller may adjust a temperature applied to the surface from the third surface temperature applied during dissipation back to the second surface temperature $T_{S2}$, or other appropriate temperature, intended to be applied during normal operation of the device.

In one implementation of the above described embodiment, in a normal operating mode of a device, a second temperature $T_{S2}$ is applied to the surface for a desired first duration. As described previously, this temperature may be applied to the surface using either a constant thermal profile and/or a variable thermal profile which may include multiple thermal pulses. After the first duration is exceeded, or if a heatsink temperature of the device meets the first threshold temperature described above, the normal operating mode of the device may be ended and a thermal dissipation mode may be applied. However, if the heatsink temperature does not reach or exceed the first threshold temperature, the device may continue to deliver the desired temperature profile for the specified duration. During the thermal dissipation mode, the third surface temperature $T_{S3}$ and corresponding thermal profile may be applied to the surface for a second predetermined duration while the heatsink dissipates the stored thermal load. When the specified duration has passed, a controller of the device may determine if the heatsink temperature is below the second threshold temperature. If the heatsink is below this threshold temperature after the second predetermined duration has expired, the controller may switch the device operation back to the normal operating mode to apply a desired thermal profile to the surface using the heating and/or cooling elements of the device. If the heatsink is still above the second threshold temperature after the specified duration, a controller of the device may delay switching back to the normal operating mode with a desired thermal profile until that condition is met.

As noted previously above, in some instances, it may be desirable to apply absolute temperatures and rates of temperature change to a user's skin such that a thermoneutral sensation is experienced by the user during the transition from a normal operating mode to a thermal dissipation operating mode of a device. This may be accomplished in a number of ways. For example, the relative temperatures and rates of temperature change of the heatsink and/or the surface the device is in contact with may both be actively controlled during a heat dissipation mode to provide a thermoneutral sensation to a user. However, depending on the particular operating parameters used, it may also be possible to provide a thermoneutral sensation to a user using more passive control methods as detailed below. In either case, the temperatures and rates of temperature change applied to a surface when transitioning to, and/or during, a thermal dissipation operating mode of a device may correspond to any appropriate combination of the temperatures and rates of temperature change described herein to provide a thermoneutral sensation to a user as the disclosure is not limited to any particular combination of temperature and/or rate of temperature change.

In one specific embodiment, a thermoneutral sensation may be provided to a user by limiting an operating temperature of the heatsink of a device such that the resulting rates of temperature change and temperature applied to a surface when transitioning between operating modes operation are applied slowly enough and/or are within appropriate ranges such that they do not induce a perceptible change in thermal sensation for the user. For example, the operation of the heating and/or cooling elements of a device may be reduced, and in some instances stopped, by a controller of the elements when a threshold heat sink temperature $T_{Th1}$ is met and/or after a predetermined duration. The heatsink may then be permitted to exchange heat, i.e. thermally equilibrate, with both the surrounding environment and the heating and/or cooling elements which will result in a temperature change in the heating and/or cooling elements and the surface they are in contact with as shown in the transition period B in FIG. 4. Assuming the relative temperature differential between the threshold heatsink temperature $T_{Th1}$ and the temperature $T_{S2}$ applied to the surface during normal operation is sufficiently small, the rate of temperature change during thermal equilibration without actively operating the heating and/or cooling elements may be sufficiently low to provide a relatively thermoneutral sensation to the user. In some embodiments, this may be viewed as permitting the temperature of the surface to "free fall" without active control over the temperature applied to the surface during thermal equilibration such that the thermal load applied to the heat sink is less than a rate of thermal dissipation of the heat sink. Once the desired temperature $T_{S3}$ to be applied to the surface during thermal dissipation is reached, the heating and/or cooling elements may be appropriately operated by the controller of the device to maintain the desired temperature and/or thermal profile applied during period C of the device operation.

In some embodiments, the rate of temperature change of the heatsink and/or surface may be monitored using one or more temperature sensors during thermal equilibration. Accordingly, if a rate of temperature change of either the heatsink and/or the surface falls outside of the desired operating windows 150 and 152 (e.g. slower than a lower threshold rate, higher than an upper threshold rate, greater than an upper threshold temperature, and/or less than a lower threshold temperature) for a given portion of the dissipation operating mode, a controller of the device may operate the heating and/or cooling elements to control the rate of temperature change and/or absolute temperature of the surface and/or heatsink. Thus, the device may be permitted to thermally equilibrate passively without actively operating the heating and/or cooling elements while the device operates within a desired set of operational boundary conditions. However, a controller of the device may actively control this thermal equilibration process using the heating and/or cooling elements during the transition period between the normal and thermal dissipation operating modes to maintain the device operation within a desired operating window to provide a desired combination of thermal sensations to a user.

The above embodiment describes permitting the temperature of a surface to "free fall" during a transition period between a normal mode of operating a device and a thermal dissipation mode of operating the device such that the thermal load applied to the heatsink is less than a rate of thermal dissipation of the heatsink. However, embodiments in which the absolute temperatures and rates of temperature change of both the heatsink and a surface the device is in contact with are actively controlled by operating the heating and/or cooling elements of the device during this transition period are also contemplated as the disclosure is not limited in this fashion.

While the above embodiments have been directed to a device that is operated to apply a cooling sensation to a user with a reduced surface temperature, and a corresponding increase in heatsink temperature, the current disclosure is not limited to only applying cooling sensations to a user. For example, as previously discussed, a thermal adjustment device may also be used to apply a warming sensation which would correspond to applying increased temperatures to the surface and reduced temperatures of the heatsink which may be less than a temperature of the surrounding ambient environment. In such an embodiment, the thermal adjustment device may still be operated in two or more operating modes to apply a desired stimulation to a user in at least a first mode and dissipate the thermal load applied to the heatsink during the second operating mode.

The above embodiments have also been described as using temperature thresholds for selectively controlling switching between the different modes of operation. However, embodiments in which different operating modes are monitored to detect when to switch between the different modes, and/or time thresholds are used to switch between the different modes, are contemplated as the disclosure is not so limited. For example, as previously described, heat flux rates, temperature differentials, and/or temperatures of components other than the heatsink may be monitored. Accordingly, it should be understood that the depicted embodiment is only exemplary and does not restrict the current disclosure to only the depicted temperature profiles and methods of operation.

It should be understood that the above embodiments may be implemented using any appropriate temperatures for the various described operating modes. For example, typical skin temperatures range from about 27° C. to about 30° C. Additionally, as elaborated on further below, cold pain perception typically begins at temperatures below about 15° C. and heat pain perception typically begins at temperatures above about 45° C. Accordingly, in some instances where a cooling sensation is applied to a user, a temperature applied to the skin of a user may be maintained between about 15° C. and 45° C., 20° C. and 40° C., or any other appropriate temperature. Additionally, when operated in a cooling mode, the normal operating temperature may be maintained between about 15° C. and 30° C., 20° C. and 30° C., 25° C. and 30° C., and/or any other appropriate temperature range. A corresponding temperature threshold of a heatsink to switch to a heat dissipation mode may be between 30° C. and 50° C., 30° C. and 40° C., 35° C. and 40° C., 40° C. and 50° C., and/or any other appropriate temperature range. Additionally, a second temperature threshold to switch back to normal operation and/or for shutdown purposes, may be between 30° C. and 40° C., 30° C. and 36° C., and/or any other appropriate temperature. The temperature applied to the underlying surface during the heat dissipation mode may also be between 25° C. and 40° C. Further, when it is desired to apply a thermally neutral or less intense cooling sensation to a user, the temperature applied to the user during the heat dissipation mode may be between 25° C. and 36° C., 30° C. and 36° C., 31° C. and 35° C. or any other appropriate temperature range. Of course, other appropriate temperature ranges both greater than and smaller than those noted above may also be implemented as the disclosure is not so limited. Additionally, embodiments in which a warming thermal sensation is applied to a user with corresponding appropriate thresholds are also contemplated.

Example: Thermal Perception

Thermal sensations on the skin (warmth or cool) are perceived through two discrete types of sensory organs—cold and warm thermoreceptors. The relative degree of stimulation of the nerve endings determine a person's perception of the intensity of a thermal sensation. The warm and cool thermoreceptors are activated in specific temperature ranges and are each uniquely sensitive to rates of temperature change. As explained further below, it is through the Inventors' understanding of the unique behavior of the two types of thermoreceptors it is possible to determine temperature profiles that enable the manipulation of a user's skin temperature in such a way that it may be modulated from a noticeably cold temperature to a temperature higher than initial skin temperature without generating meaningful sensations of warmth. However, embodiments in which a temperature of a user's skin is reduced from a warmer temperature to a lower temperature without generating meaningful sensations of cooling are also contemplated.

Figure 6:
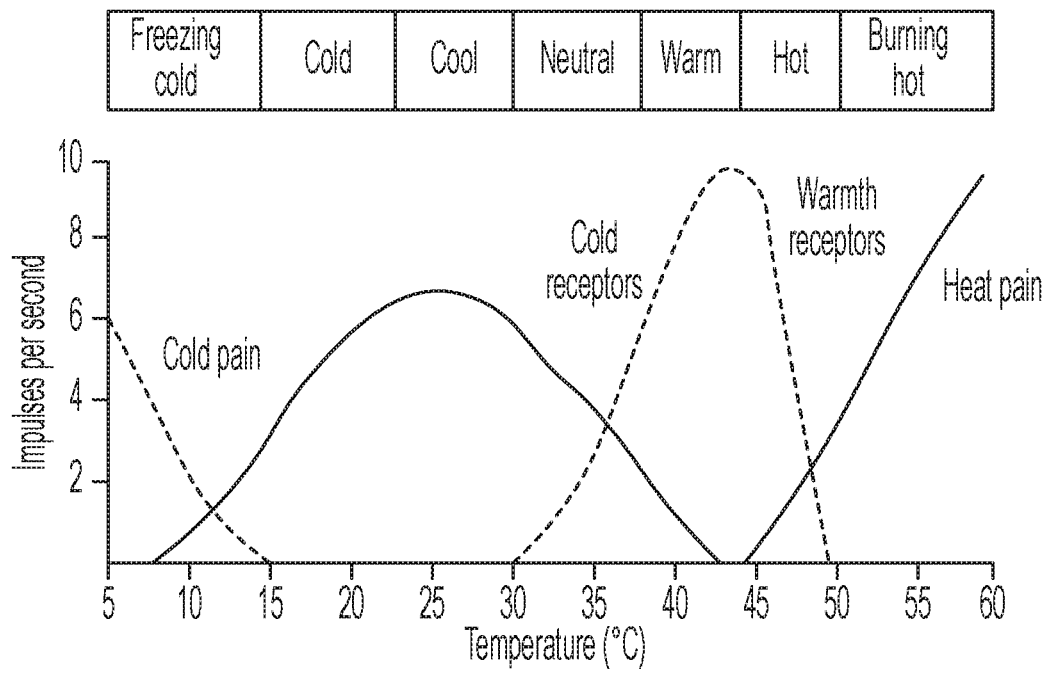
FIG. 6 is a graph of different forms of temperature perception.

FIG. 6 shows the temperature ranges over which cold and warm thermoreceptors are sensitive. Specifically, the discharge frequencies of 4 types of nerve endings in the human skin, cold thermoreceptors, warmth thermoreceptors, as well as cold and hot pain nerve fibers are shown at different temperatures. FIG. 6 is reproduced from Hall, J. E., and Guvton, A. C. *Textbook of Medical Physiology*, 11th Ed. Saunders Elsevier, pp. 608, FIG. 48-10, 2011. FIG. 6 has been included for the purposes of illustrating the overlapping ranges of cold and warmth thermoreceptors as well as hot and cold pain perception over these temperatures. As shown in the figure, cold thermoreceptors are most sensitive at temperatures around 25° C. but their active range spans from around 15° C. up to over 40° C. Below 15° C. the sensation becomes dominated by pain receptors that are activated. Warm thermoreceptors are sensitive from about 30° C. up to the warm pain threshold at about 45° C. Innocuous (non-painful) sensations of warmth are typically generated at static temperatures of about 37-42° C. Therefore, it should be noted that below about 30° C., the temperature of a user's skin may be increased without generating sensations of warmth because the warm thermoreceptors are not sensitive in that temperature range. Accordingly, in some embodiments, when it is desired to increase the temperature of a user's skin during a heat dissipation operating mode, the temperature applied to the user's skin, or other underlying surface, may be increased at a first average rate at temperatures below a threshold temperature and at a second average rate that is greater than the first average rate at temperatures above the threshold temperature. For example, due to the rate insensitivity at lower temperatures, a device may simply be permitted to thermally equilibrate without driving the system to reduce the temperature change applied to a user's skin Specifically, the one or more heating and/or cooling elements of a system may simply be shut off or driven at a reduced amount prior to the threshold temperature being applied to the user's skin. After approaching or meeting the threshold temperature, the system may be operated to control the rate of temperature change applied to the user to avoid the perception of unwanted thermal sensations as detailed above. Depending on the particular embodiment, the threshold temperature may be between or equal to about 28° C. and 32° C., 29° C. and 31° C., and/or any other appropriate threshold temperature including for example a threshold temperature of about 30° C. The rate sensitivity for perception of warming thermal sensations for temperatures above 30° C. is detailed further below.

Even in temperature ranges where thermoreceptors are sensitive, the thermoreceptors exhibit strong time-dependent behavior. Specifically, thermoreceptors respond more strongly to faster rates of temperature change (i.e. increased thermal perception) and will adapt over time to static temperature profiles (i.e. decreased thermal perception). Therefore, a controller of a thermal adjustment system may control both a temperature as well as a rate of temperature change to provide either a cooling or neutral thermal sensation to a user while increasing a temperature of the user's skin for skin temperatures greater than or equal to the above noted threshold temperatures such as a threshold temperature of about 30° C. For example, both warm and cold of thermoreceptors exhibit increased firing rates if the temperature is changing at rates greater than about 0.1° C./s, but cold thermoreceptors exhibit a notably heightened sensitivity to rates of temperature change compared to warm thermoreceptors.

Figure 7:
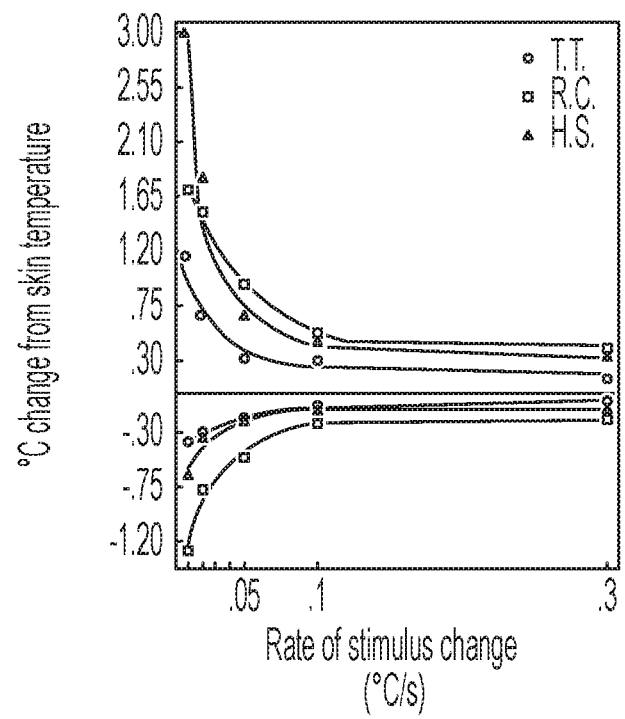
FIG. 7 is a graph of temperature change from skin temperature versus rate of temperature change for thermal perception by a subject.

FIG. 7 is included to illustrate the rate dependence of thermal perceptions of a person. Further, this figure has been reproduced from Kenshalo D R, Holmes C, Wood P. *Warm and cool thresholds as a function of rate of stimulus temperature change*. Percept Psychophys 3, pp. 81-84, 1968. The figure depicts the threshold temperature changes from a baseline skin temperature of 31.5° C. on the dorsal surface of the forearm of three participants to detect a warming or cooling sensation. The applied temperature changes were increased or decreased with rates of change of 0.3° C./s, 0.1° C. is, 0.05° C./s, 0.02° C. Is, and 0.01° C./s. As shown in the figure, the determined thermal thresholds for both perceived cool and warm sensations varied significantly according to the rate of change of the temperature applied to the user. Specifically, FIG. 7 shows that slower rates of temperature change are associated with higher magnitude temperature changes relative to the initial skin temperature for perception of either a cooling or warming sensation. As shown in the figure, this rate sensitivity effect was particularly evident for rates of temperature change lower than 0.1° C./s and was more pronounced for the perception of warming sensations as compared to the perception of cooling sensations. Without wishing to be bound by theory, the perception of cooling sensations is more sensitive to rapid temperature changes while warming sensations are less sensitive to the rate of temperature change. Therefore, the perception of warming sensations may be more prone to adaption, i.e. lower thermal perception, if the applied rates are sufficiently slow. Conversely, due to the increased rate sensitivity of cold thermoreceptors, it may be desirable in some embodiments to cool a surface from a higher warming temperature at a rate slower than that applied during warming from a lower cooling temperature to avoid the perception of unwanted thermal sensations.

Adaptation to thermal sensations can occur over a wide range of temperatures, though it is easiest in the range of temperatures that are typically observed in human skin under ambient conditions from about 30° C. to 36° C. In either case, by appropriately controlling the rate of temperature change within corresponding temperature ranges, it may be possible to adjust a temperature of a user's skin while providing a substantially neutral thermal sensation to the user in either the cooling and/or warming directions of temperature adjustment. For example, this may be especially useful when warming a user's skin to operate a thermal adjustment device in a heat dissipation mode where the faster rate of physiological adaptation to warming permits the device to warm the user's skin to temperatures greater than an initial skin temperature of the user without generating sensations of warmth.

In view of the above, in one embodiment, when warming from a cooling sensation, an average temperature change rate below a threshold temperature may be between or equal to about 0.5° C./s and 1.0° C./s 0.5° C./s and 5° C./s, 10° C. is and 10° C./s, 5° C./s and 10° C./s, and/or any other appropriate temperature change rate. Correspondingly, above the threshold temperature the applied temperature change rate may be less than or equal to 1° C./s, 0.5° C./s, 0.1° C./s, 0.05° C./s, and/or any other appropriate temperature change rate. In some embodiments, the threshold temperature may correspond to those temperatures detailed previously above.

In contrast to warming from a cooling sensation, going in the opposite thermal direction, i.e. cooling from a higher temperature to a lower temperature, may not be perceived in the same manner as noted above. Specifically, due to cold thermoreceptors being active above 40° C., and the heightened rate sensitivity of cold thermoreceptors, possible perceptions of a cooling sensation may occur during most, if not all of, a cooling process depending on the rate of cooling applied to a person. Accordingly, when cooling from a first higher temperature to a second lower temperature it may be desirable to maintain a relatively low rate of temperature change to avoid the generation of unwanted cooling sensations for a user. Appropriate rates of temperature change during cooling may be less than or equal to 1° C./s, 0.5° C./s, 0.1° C./s, 0.05° C./s, 0.01° C./s, and/or any other appropriate temperature change rates.

Figure 8A:
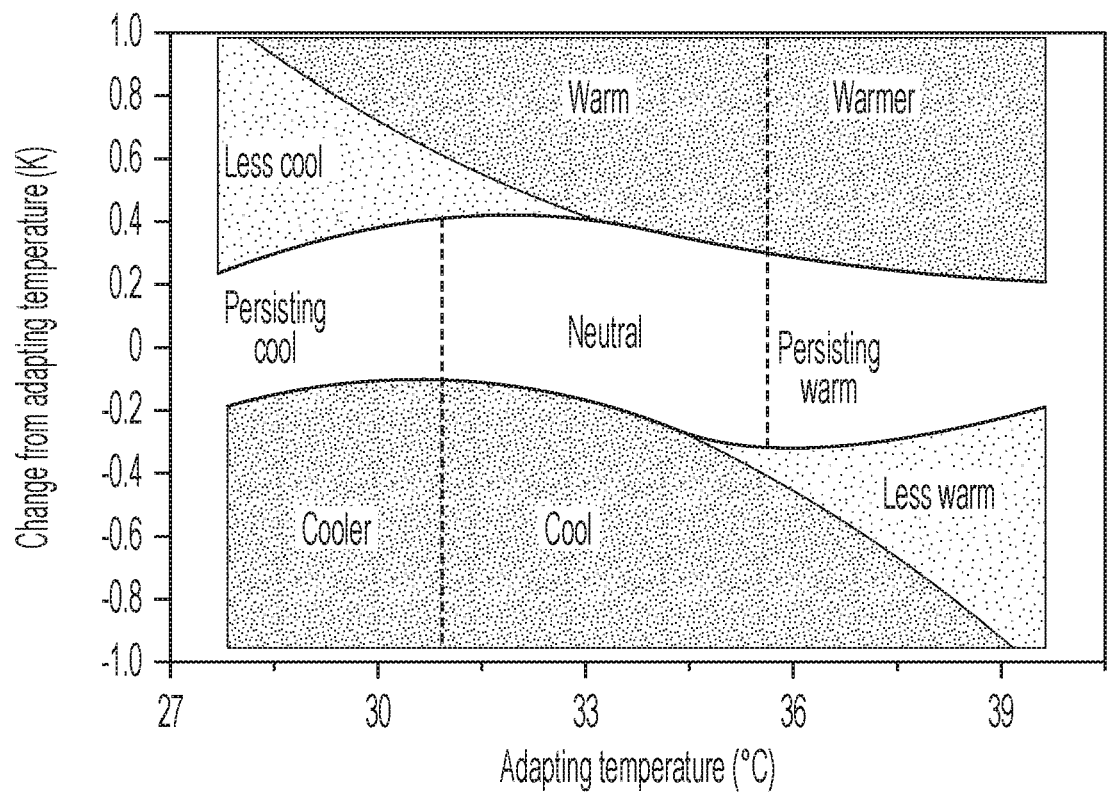
FIG. 8A is a graph of temperature perceptions by an individual for changes from an adaptation temperature versus the adaptation temperature.

FIG. 8A is included for the purpose of illustrating the thermal sensations experienced by a person due to the interplay between the temperature a person's skin is thermally adapted to and temperature changes applied to the user' skin relative to that adaptation temperature. FIG. 8A is reproduced from Kenshalo, D. R. *Psychophysical studies of temperature sensitivity*. in W. D. Neff (Ed). *Contributions to sensory physiology*. New York: Academic Press, pp. 19-74, 1970. The figure is a graph that depicts temperatures that a person's skin has thermally adapted to versus changes from the adaptation temperature to provide a specific type of thermal perception. For example, for temperatures between about 31° C. and 35° C. temperature changes from the thermal adaptation temperature that are less than or equal to about 0.4° C. and 0.2° C. produce relatively neutral thermal sensations. This is in contrast to temperatures below about 30° C. or 31° C. which may be associated with lesser or greater amounts of a cooling thermal sensation and temperatures above about 36° C. which may be associated with lesser or greater amounts of a warming thermal sensation.

Figure 8B:
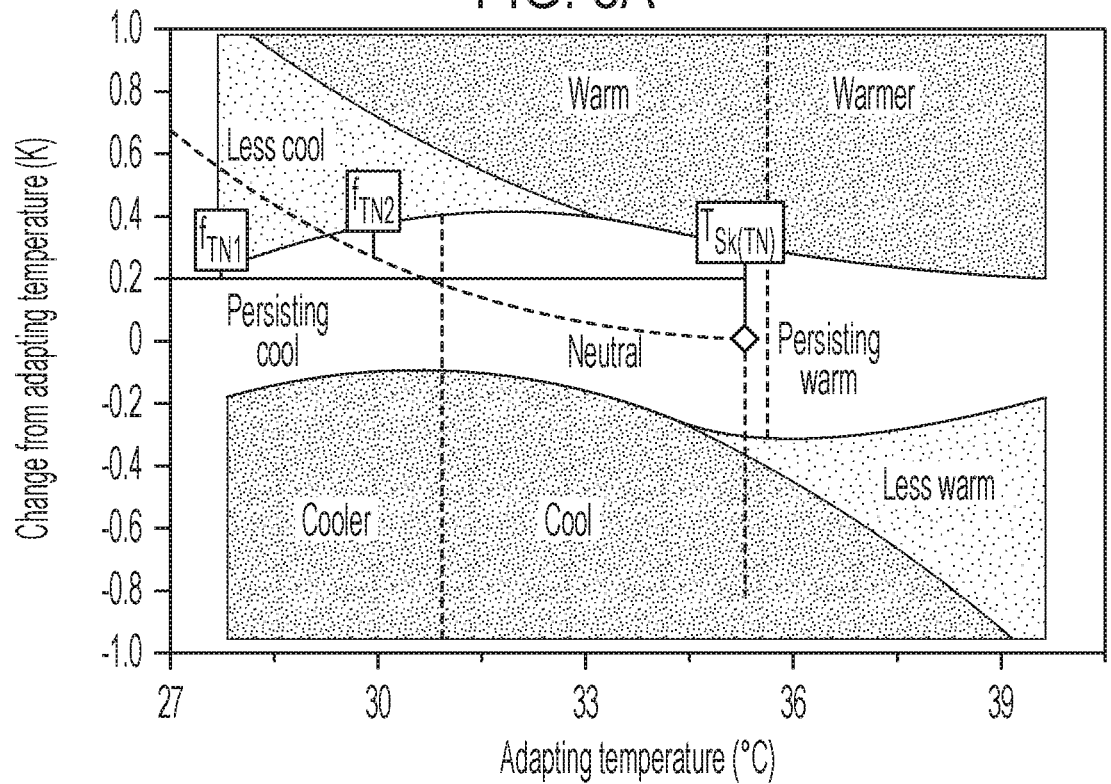
FIG. 8B is a graph depicting several temperature profiles overlaid on the graph of temperature perceptions of FIG. 8A that result in the perception of neutral thermal sensations by a user.

FIG. 8B is a modified version of FIG. 8A with two temperature profiles $F_1$ and $F_2$ overlaid on the graph depicting ways to increase the temperature of a user's skin while providing either a reduced amount of perceived cooling and/or a neutral thermal sensation during at least a portion of the temperature profile. The depicted temperature profiles may increase a temperature of the user's skin from a first cooler temperature to a target skin temperature $T_{Sk(TN)}$ without generating sensations of warmth by controlling the rate of temperature change which may be related to the change from thermal adaptation of the user's skin. Additionally, due to the skin being less sensitive to warming sensations below about 30° C., larger temperature changes relative to an adaptation temperature, i.e. faster rate of temperature change, may be applied at temperatures below about 30° C. which is depicted by the differences between the two illustrated temperature profiles. Of course, in addition to the above, based on the physiology of thermosensation, there is an upper limit to the temperatures that may be applied to a user's skin while maintaining a neutral thermal sensation, above which the user may notice warmth regardless of the rate of temperature change. This physiological limit has been identified to be at temperatures above about 36° C. Thus, in some embodiments where the temperature of a device is increased to provide a neutral thermal sensation to a user, the temperature applied to a user's skin may be maintained below about 36° C.

It should be noted that FIGS. 8A and 8B do not depict a rate of temperature change versus adaptation temperature. Instead, they only depict a threshold temperature change at which a subject first perceived a thermal sensation. However, larger threshold temperatures may be associated with larger rates of temperature change, and thus these figures are informative for a discussion of temperature profiles that may be applied to provide various types of thermal stimulation. Accordingly, even though not directly depicted in the figures, it should be understood that the depicted temperature profiles $F_1$ and $F_2$ may have appropriate temperature change rates selected to avoid the perception of unwanted thermal sensations, which in the depicted embodiment, would correspond to warming thermal sensations.

While reduced cooling sensations and/or a neutral sensation during warming of a user's skin has been depicted in the figure and described above, the current disclosure is not limited in this fashion. For example, as previously described, instances where reduced warming sensations and/or a neutral thermal sensation may be applied to a user during cooling of the user's skin from an elevated temperature are also contemplated.

Example: Balancing Heat Dissipation and Generation

An example of the various parameters that may be monitored and controlled, as well as the resulting system behavior is provided below relative to a wearable thermal adjustment device that includes a passive heatsink and thermoelectric module. The example includes discussion of operating the system using successive cycles of a cooling operating mode and a heat dissipation operating mode. Specifically, methods of controlling a device based on inputs from various sensors in a closed-loop system are described.

Figure 9A:
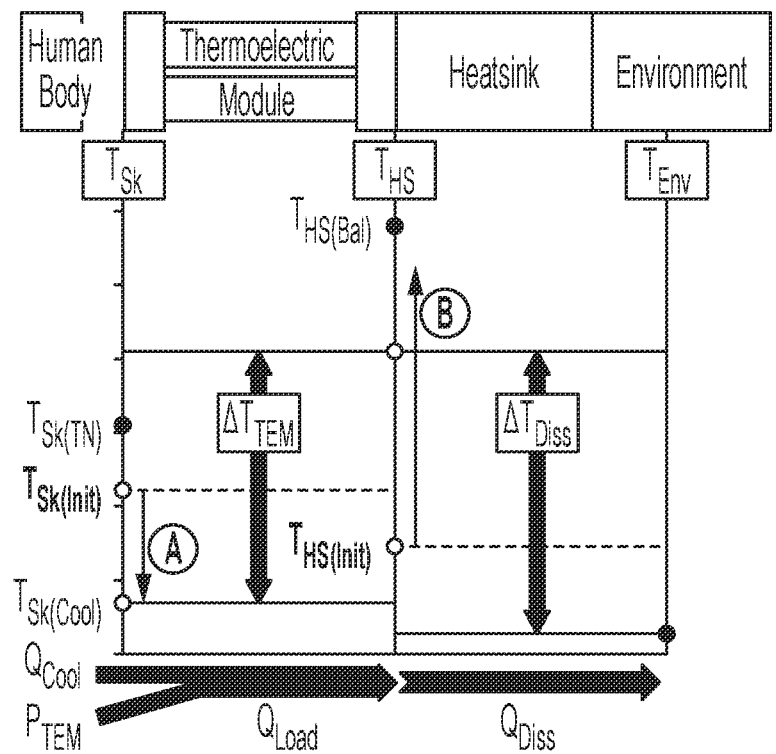
FIG. 9A is a schematic diagram of an active cooling process for a thermoelectric system coupled to a heatsink.
Figure 9B:
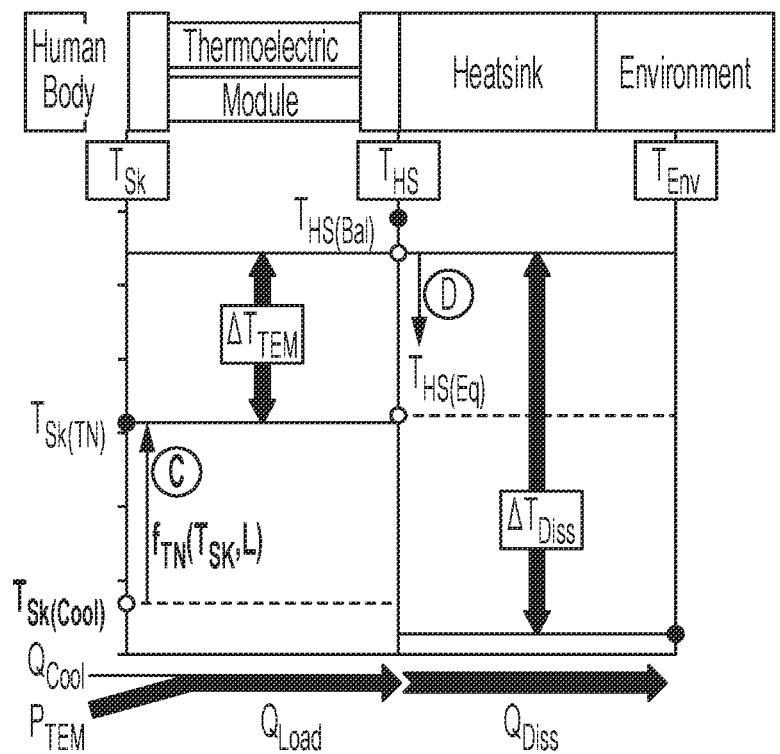
FIG. 9B is a schematic diagram of a thermal equilibration process of the heatsink for the system of FIG. 9A after active cooling.

FIGS. 9A and 9B, depict a simplified model of a temperature adjustment device being used to cool a person during different modes of operation including active cooling and thermal dissipation respectively. Specifically, the model includes four layers corresponding to the human body, a thermoelectric module, a passive heatsink, and the surrounding ambient environment. The model is simplified to emphasize the mechanisms relevant to the processes and methods disclosed herein. Specifically the model is directed to managing the amount of heat pumped into the heatsink ($Q_{Local}$) as related to the rate of heat dissipation into the environment ($Q_{Diss}$). As will be discussed further below, this balance is dictated by managing the temperature difference across the thermoelectric ($\Delta T_{TEM}$) as it is related to the temperature difference between the heatsink temperature and the temperature of the surrounding ambient environment $\Delta T_{Env}$.

In general terms, during active cooling the skin temperature $T_{Sk}$ is controllably cooled to $T_{Sk(Cool)}$, which may be a fixed or variable temperature. While operating under this active cooling condition the thermal load $Q_{Load}$ is applied to the heatsink and heat is dissipated from the heatsink at a rate $Q_{Diss}$. Due to $Q_{Load}$ being greater than $Q_{Diss}$. The heatsink temperature $T_{HS}$ increases during active cooling. When $T_{HS}$ reaches a defined threshold, e.g. a maximum heatsink temperature $T_{HS-MAX}$, the system may switch to the heat dissipation mode of FIG. 9B.

In FIG. 9B, the skin temperature $T_{Sk}$ may be increased along a thermoneutral temperature profile $f_{TN}$ until it is equal to a desired temperature $T_{SK(TN)}$. This gradually reduces the temperature differential across the thermoelectric module $\Delta T_{TEM}$, which in turn reduces the thermal load generated by the thermoelectric module $Q_{Load}$. As detailed further below, the various operating parameters may be selected such that the thermal load is less than the rate of heat dissipation of the heatsink at this temperature. Accordingly, the heat sink temperature may decrease until a second heatsink temperature threshold $T_{HS(Eq)}$ is reached after which the system may simply turn off and relax back to the initial conditions and/or return to active cooling.

In developing the following model, several simplifying assumptions were made. Specifically, the effects of thermal interface resistance were neglected by assuming the same temperature across the thermal interfaces. In the model, the temperature of the skin ($T_{Sk}$) is treated the same as the temperature of the cold side of the thermoelectric ($T_{Cold}$), and the temperature of the heatsink ($T_{HS}$) is treated as the same as the temperature of the hot side of the thermoelectric ($T_{Hot}$).

The passive heatsink may be made from a material with high thermal conductivity, typically aluminum, copper, or other thermally conductive material such as a different metal, combination of metals, or thermally conductive polymers or textiles. In either case, for purposes of the current model, it was assumed that there was perfect conduction through the heatsink. Assuming perfect conduction means that the temperature of the surface of the heatsink ($T_{Surf}$) was assumed to be the same as the temperature of the heatsink ($T_{HS}$), which is the same as the temperature of the hot side of the thermoelectric ($T_{Hot}$). However, in reality, the temperature of the surface of the heatsink will depend on the geometry of the heatsink and how that relates to local rates of thermal dissipation and conduction.

The current model also ignores the adaptive behavior of the human body in response to localized cooling. However, in reality, the thermal properties of the human body are locally modulated through vasoconstriction and vasodilation in response to localized heating and/or cooling. Therefore, this model does not take into account the complex and adaptive thermal properties of the human body itself which do not have a large impact on the method/process disclosed. In some embodiments though, the physiological behavior of the human body may be accounted for in the selection (or modulation) of the skin temperature during active cooling.

As shown in the figure, during thermoelectric cooling, external power ($P_{TEM}$) may be provided to the thermoelectric module to drive a heat flux ($Q_{Cool}$) from the cold side of the thermoelectric to the hot side. $Q_{Cool}$ is the heat that is pumped through the heatsink and corresponds to a combination of competing processing including Peltier cooling that removes heat from the human body as well as the Thompson effect which is small and may be ignored, heat conduction from the hot side to the cold side of the thermoelectric, and Joule heating. $P_{TEM}$ is the power provided to the thermoelectric module to move heat from the skin to the heatsink. This power is then converted into waste heat, which adds to the thermal load transmitted to the heatsink ($Q_{Load}$). Therefore, the thermal load on the heatsink may be the sum of the heat moved from the skin to the heatsink and the power required to do so, see equation below and the combined heat flow arrows in FIG. 9A.

$$Q_{Load} = Q_{Cool} + P_{TEM}$$

FIG. 9A depicts an operating mode in which the thermal load applied to the heatsink $Q_{Load}$ is greater than the heat dissipation rate of the heatsink $Q_{Diss}$. Such an operating mode may occur during active cooling as shown in the figure. This imbalance in thermal load and dissipation rate leads to an increasing temperature differential across the thermoelectric $\Delta T_{TEM}$ due to the increasing heatsink temperature $T_{HS}$. As noted previously, thermoelectric materials are less efficient as the temperature difference across the thermoelectric increases. Therefore, the efficiency of the thermoelectric module will decrease as the temperature differential $\Delta T_{TEM}$ increases which will increase the thermal load applied to the heatsink. Thus, this operating mode may result in a positive feedback loop that leads to the heatsink increasing in temperature even when a constant temperature is applied by the system. This type of behavior presents a control challenge because, as presented in more depth below, the rate of thermal dissipation of the heatsink also increases with increasing heatsink temperature.

A passive thermally conductive heatsink dissipates heat into the surrounding environment ($Q_{Diss}$) through a combination of natural convection and radiative cooling.

$$Q_{Diss} = D_{Convection} \pm Q_{Radiation}$$

Which thermal dissipation process is dominant, however, depends strongly on the geometry, material selection, temperature of the heatsink, and specific environment of the heatsink. If it is assumed that the environmental temperature remains fixed, the rate of thermal dissipation increases with $T_{HS}$. Specifically, thermal dissipation associated with natural convection increases linearly with a temperature difference between the heatsink and temperature of the environment $\Delta T_{Diss}$ and radiative cooling increases as a difference between $T_{HS}^4$ and $T_{Env}^4$. Therefore, the precise relationship between $Q_{Diss}$ and the heatsink temperature will depend strongly on the design of the heatsink and the environment the heatsink is located in.

Having described the various operating parameters that are applicable to the current model, operation of a system during the active cooling and heat dissipation modes of operation shown in FIGS. 9A and 9B is described further below respectively.

Referring to FIG. 9A, when the device is worn but not turned on, the heatsink temperature ($T_{HS(Init)}$) is somewhere between the initial skin temperature ($T_{Sk(Init)}$) and the environmental temperature ($T_{Env}$). When the system is turned on a temperature sensor on the cold side of the thermoelectric may provide feedback to a PID control system that modulates $P_{TEM}$ such that the user's skin is cooled from the initial skin temperature $T_{Sk(Init)}$) to a second cooler temperature $T_{Sk(Cool)}$. This process is labelled (A) in FIG. 9A. Initially during active cooling, the thermal load on the heatsink ($Q_{Load}$) is much greater than the rate of thermal dissipation ($Q_{Diss}$) because the heatsink temperature $T_{HS}$ is similar to the environment temperature $T_{Env}$. Therefore, as shown by the relative sizing of the arrows, the thermal load applied to the heatsink $Q_{Load}$ is greater than the thermal dissipation rate $Q_{Diss}$ which causes the heatsink temperature $T_{HS}$ to gradually increase. As $T_{HS}$ continues to increase, labelled (B) in FIG. 9A, the heat dissipation rate $Q_{Diss}$, power applied to the thermoelectric $P_{TEM}$, and heat transferred from the user's skin to the heatsink $Q_{Load}$ all increase as well. Therefore, the system is both consuming and dissipating more power as a result of the elevated heatsink temperature. For most wearable thermoelectric systems, this positive feedback loop leads to continually increasing $T_{HS}$ until a maximum $\Delta T_{TEM}$ of the thermoelectric is reached, determined by the thermoelectric module and the available power. In conventional operation, the device is typically shut off or removed from the body before this temperature is reached. Alternatively, depending on the environmental conditions and the design of the heatsink, it may be possible that at some elevated heatsink temperature the thermal load the heatsink and the dissipation rate may be equal permitting steady-state operation of the system at an elevated temperature. However, even if such a condition were to occur, maintaining a desired thermal sensation applied to a user when shutting down the system would still be a challenge and may benefit from implementation of the methods and systems disclosed herein.

It is worth emphasizing that, while the increase in $T_{HS}$ may drive the increase in $\Delta T_{TEM}$ and $\Delta T_{Diss}$, the heat dissipation rate from the passive heatsink $Q_{Diss}$ may be a controlling parameter in the heat transfer process that dictates the rate at which the temperature of the heatsink increases. However, $Q_{Diss}$ depends, on environmental conditions that are regularly changing during the use of a wearable thermoelectric system. Therefore, the heat dissipation method described relative to FIG. 9B below may also take into account the rate of thermal dissipation into the environment from the heatsink during operation in addition to taking into account the amount generated during operation in order to successfully cool the heatsink to a desired operating temperature.

As noted above, during active cooling, which may correspond to a normal operating mode of a wearable thermoelectric system with a passive heatsink, the thermal load applied to a heatsink may be greater than the rate of thermal dissipation from the heatsink (i.e. $Q_{Load} \geq Q_{Diss}$) and the corresponding heatsink temperature may be greater than the initial heatsink temperature (i.e. $T_{HS} > T_{HS(Init)}$) due to the considerable excess heat stored in the heatsink. However, as detailed further below relative to FIG. 9B, if the heatsink temperature and temperature difference across the thermoelectric module are appropriately controlled, it may be possible to dissipate the heat accumulated in the heatsink and return the system to steady state operation at a lower heatsink temperature. Further, as described above, this process may be conducted while providing either reduced cooling sensations and/or a neutral thermal sensation to a user without requiring that the device be removed from the body to cool down.

FIG. 9B illustrates an operating mode for dissipating thermal energy from the heatsink while maintaining a desired temperature applied to a user of a thermal adjustment device including a passive heatsink. As shown in the figure, during process (C) the skin temperature $T_{Sk}$ may be increased to a warmer skin temperature $T_{Sk(TN)}$ from the active cooling set point $T_{SK(Cool)}$ along a temperature profile $f_{TN}$, which may be a function of skin temperature versus time, and in some embodiments, may be a neutral thermal sensation profile as previously described. This increased skin temperature corresponds to a decreased temperature differential across the thermoelectric material $\Delta T_{TEM}$ and may be selected such that the thermal load applied to the heatsink is less than the thermal dissipation rate the of the heatsink (i.e. $Q_{Load} < Q_{Diss}$) which may still be large due to the elevated heatsink temperature. During process (D) the heatsink temperature $T_{HS}$ begins to decrease towards a desired steady state operating temperature $T_{HS(Eq)}$ which may be greater than the temperature applied to the skin during thermal dissipation. Due to the thermoelectric material's efficiency increasing with the decreased temperature differential, this may initiate a negative feedback loop that enables complete thermal discharge of the heatsink to a desired threshold state while maintaining a desired temperature applied to the skin of a user.

In view of the above, a condition for successful thermal dissipation of a system may be simply stated as:

$$\text{When } T_{Sk}=T_{Sk(TN)}, Q_{Load} < Q_{Diss}$$

Accordingly, restating the above successful thermal dissipation of a heatsink may occur when the temperature applied to the skin by a thermal adjustment device is raised to the appropriate operating temperature such that the temperature differential across the thermoelectric ($\Delta T_{TEM} = T_{HS} - T_{Sk}$) has been sufficiently reduced such that the thermal load applied to the heatsink, $Q_{Load}$, which may be a function of the temperature differential, is less than the thermal dissipation heatsink $Q_{Diss}$. If these conditions are met then the heatsink temperature may begin to decrease initiating the above noted negative feedback loop that permits the thermal system to relax to a desired operating temperature. The process is the reverse of the positive feedback loop observed during active cooling and may be continued until the heatsink temperature is equal to the skin temperature applied, or other desired temperature, during this thermal dissipation of operation (i.e. $T_{HS} = T_{Sk} = T_{Sk(TN)}$), at which point $\Delta T_{TEM} = 0$ and $P_{TEM} = 0$. At this point, the close-loop thermoelectric device has effectively turned itself off while maintaining a desired skin temperature. Therefore, without any additional power provided to the system, the thermoelectric cooling system may be allowed to continue to relax, until it has returned to its initial state ($T_{Sk(Init)}$, $T_{HS(Init)}$. Alternatively, the system may be returned to a normal operating mode such as active cooling as previously described.

Based on the above framework, it is also possible to define operating limits for the thermal dissipation of a system operated in manner described herein. Specifically, if the relationship between the heatsink temperature and the temperature applied to the skin during thermal dissipation properly balanced it may lead to the following condition:

$$\text{When } T_{Sk}=T_{Sk(TN)}, Q_{Load} \geq Q_{Diss}$$

Restating the above, in some operating modes a temperature applied to the skin by a system may result in a temperature differential across a thermoelectric material such that thermal load applied to the heatsink may be greater than or equal to the thermal dissipation rate of the heatsink which may cause the heatsink temperature to either remain constant ($Q_{Load} = Q_{Diss}$) or continue to increase ($Q_{Load} > Q_{Diss}$). Therefore, an upper limit for the heatsink temperature may be defined at the point at which the thermal load is equal to the thermal dissipation rate from the heatsink temperature for a given temperature applied to the skin of a user during thermal dissipation $T_{HS}$ (i.e. $Q_{Load} = Q_{Diss}$ when $T_{Sk} = T_{Sk(TN)}$). This temperature may be referred to as $T_{HS(Bal)}$ in FIGS. 9A and 9B because the thermal load on the heatsink is balanced with the rate of thermal dissipation into the environment. Therefore, a thermal adjustment device may be capable of dissipating heat from the heatsink, and/or may operate continuously, so long as the heatsink temperature $T_{HS}$ remains conservatively below $T_{HS(Bal)}$.

As discussed previously, the rate of thermal dissipation into the environment, $Q_{Diss}$, is very sensitive to environmental conditions and these conditions are not actively controlled with a passive heatsink. However, the disclosed systems are capable of precisely controlling the temperature applied to the skin of a user and thus may modulate the heatsink temperature. However, it is challenging in practice to know $Q_{Diss}$ or what the appropriate $T_{HS(Bal)}$ is at any given time. Therefore, to enable the thermal dissipation of a heatsink, several possible operating methods may be applied.

In one embodiment, conservative assumptions may be made about the range of environmental conditions that a thermal adjustment device including a passive heatsink may be operated in. If the system is meant to be operated within a defined range of environmental conditions, then a maximum allowed heatsink temperature, $T_{HS-MAX}$, may be defined such that when the heatsink temperature is equal to the maximum allowed heatsink temperature (i.e. $T_{HS} = T_{HS-MAX}$) the system may switch from normal operation, such as a cooling mode, to a thermal dissipation operating mode in which the skin temperature of the user is adjusted to the desired temperature to enable thermal dissipation of the heatsink. Such a method may be advantageous in that it is (i) straightforward to implement and (ii) relatively robust under the desired range of operating conditions. However, possible disadvantages may include (i) unnecessarily limiting the amount of active cooling that can be provided at a given time, and (ii) the thermal dissipation of the heatsink may fail if the local environment of the thermal adjustment device is sufficiently outside the expected operating conditions such that the heat dissipation rate of the heatsink is much less than the expected range of values.

In another embodiment, the rate of temperature change of the heatsink ($dT_{HS}/dt$) may be used to estimate the instantaneous value of $Q_{Diss}$, and may be easily measured using a number of different types of temperature sensors. Without wishing to be bound by theory, the rate of heatsink temperature increase is related to the ratio of the difference between the thermal load applied to the heatsink $Q_{Load}$ and the rate of thermal dissipation $Q_{Diss}$ with the heat capacity of the heatsink ($C_{HS}$)

$$dT_{HS}/dt = (Q_{Load} - Q_{Diss})/C_{HS}$$

The heat capacity of the heatsink, $C_{HS}$, is a fixed material property that is straightforward to calculate or measure for a given heatsink. Leveraging the above relationship, the rate of temperature change and the thermal load applied to the heatsink may be used to estimate $Q_{Diss}$ at any given time, overcoming the many complications associated with environmental variability, radiative cooling, and natural convection. The temperature applied to the skin, and corresponding heatsink temperature may then be controlled appropriately to provide the desired relationship between the thermal load applied to the sink and the thermal dissipation rate to permit the heatsink to dissipate the stored heat and relax to a desired lower operating temperature.

$Q_{Load}$ may be determined in a number of different ways depending largely on what additional information is being monitored or collected by the system during operation. As noted previously, the thermal load applied to a heatsink $Q_{Load}$ may be equal to the power provided to the thermoelectric module $P_{TEM}$ and the heat transfer across the thermoelectric model from the skin of a user to the heatsink $Q_{Cool}$. Each of these three terms can be either directly measured by the system or indirectly approximated based on other system information. For example, in one embodiment, a heat flux sensor may be integrated at the interface between the thermoelectric and the heatsink to provide direct measurement of $Q_{Load}$. In another embodiment, the power electronics of a system may be designed to allow for direct measurement of the power being provided to the thermoelectric $P_{TEM}$ through some combination of the voltage across the thermoelectric module ($V_{TEM}$), the current provided to the thermoelectric module ($I_{TEM}$), and the resistance of the thermoelectric module ($R_{TEM}$). In yet another embodiment, the relevant subcomponents of $P_{TEM}$ ($V_{TEM}$, $I_{TEM}$, $R_{TEM}$) could be estimated without direct measurement to provide an estimate of $P_{TEM}$. For instance, $V_{TEM}$ may be approximated based on knowledge of the power supply being used to drive the thermoelectric, and $R_{TEM}$ may be approximated based on knowledge of the properties of the thermoelectric module and $\Delta T_{TEM}$, as measured by temperature sensors. In still another embodiment, a closed-loop PID control system may modulate power to a thermoelectric using pulsed-width modulation (PWM) with a duty cycle that can be used to approximate $I_{TEM}$ which may be taken in combination with known or estimated $R_{TEM}$ and $V_{TEM}$ of the system to estimate $P_{TEM}$. It may also be desirable in some embodiment to simply directly measure $Q_{Cool}$ using a heat flux sensor integrated at the interface between the thermoelectric and the skin. It may also be possible to approximate $Q_{Cool}$ based on the known properties of the specific thermoelectric module being used combined with knowledge of $\Delta T_{TEM}$ and an estimate or measurement of $P_{TEM}$.

In addition to the above, a maximum heatsink temperature, which may correspond to a threshold temperature for initiating heat dissipation, may be determined based on the expected thermal load applied to the heatsink when the heatsink is at the maximum heatsink temperature and the thermal adjustment device is applying a desired temperature to the skin for heat dissipation purposes including, for example, a temperature greater than that applied during a normal cooling operation. In the above described methods, the skin temperature may be held constant during thermal dissipation. Therefore, the thermoelectric is not actively cooling the skin but just maintaining a particular temperature difference across the thermoelectric which may be equal to the difference between the heatsink temperature and temperature applied to the skin (i.e. $\Delta T_{TEM} = T_{HS-MAX} - T_{Sk(TN)}$). Therefore $Q_{Cool}$ is negligible compared to $P_{TEM}$ and the thermal load applied to the sink may be assumed to be approximately equal to the power input to the thermoelectric. As noted above, the power input to the thermoelectric module $P_{TEM}(\Delta T_{TEM})$ may be determined based on the known properties of the thermoelectric module. This may then be used such that for a given thermal dissipation rate $Q_{Diss}$ and applied skin temperature during heat dissipation $T_{Sk(TN)}$, it is possible to define a maximum heatsink temperature $T_{HS-MAX}$ such that the thermal load applied to the heatsink is less than the thermal dissipation rate from the heatsink (i.e. $Q_{Load} < Q_{Diss}$).

Based on the forgoing, a maximum heatsink temperature, or threshold temperature, for switching to a heat dissipation operating mode may either be a predetermined threshold value or it may be dynamically determined based on the determined rate of temperature change of the heatsink and other relevant operating parameters of the system. Of course, in either case, the system may include a factor of safety to ensure that determined maximum permitted heatsink temperature does not exceed an absolute maximum heatsink temperature that permits the system to dissipate heat and relax to a desired lower temperature.

The above embodiments have been primarily described as being a function of heatsink temperature and thus the heat dissipation rate $Q_{Diss}$. However, embodiments in which different control strategies are implemented to appropriately control and balance the various temperatures and thermal loads are also contemplated. For example, as previously noted, in another embodiment the duration of normal operation, such as active cooling, and/or the duration of thermal dissipation may be set for fixed durations that are chosen based on assumptions about the operating conditions of the system to keep a heatsink temperature below a maximum permissible heatsink temperature to permit thermal dissipation as described above. In some instances, the timing cycle may be interrupted if temperatures of a heatsink greater than those expected are reached including for example, a temperature of the heatsink reaching a predefined maximum threshold temperature. In such an instances, the device may then switch to a thermal dissipation operating mode.

Example: Thermal Dissipation and Relaxation of a Heatsink

A thermal adjustment device was used to conduct both successful and unsuccessful thermal dissipations of an associated heatsink. The experimental system was similar to the embodiments described herein and included a thermoelectric module, multiple temperature sensors, a passive heatsink, a power supply, and a closed-loop control system for generating precise skin temperature profiles while managing the temperature of the heatsink. The passive heatsink was made from machined 6063 aluminum alloy with a specific heat capacity of 0.9 J/g-° C. and thermal conductivity of 200 W/m-K. The thermoelectric module was mounted to the aluminum alloy heatsink using thermally conductive epoxy. The outer surface area of the heatsink was 26 cm². Based on ANSYS simulations, the figure of merit for the heatsink was between 20-30° C./W under ambient temperatures between 20-40° C. with only buoyancy-driven airflow. The custom thermoelectric module had the following metrics presented in Table 1 below which were measured at a temperature of 27° C. at the hot side of be thermoelectric module under nitrogen at 1 atm.

TABLE I

| Figure of Merit | Value (Nitrogen, 1 ATM) |
| --- | --- |
| $V_{MAX}$ (V) | 14 |
| $\Delta T_{MAX}$ (° C.) | 57 |
| $I_{MAX}$ (A) | 2 |
| $Q_{MAX}$ (W) | 18 |
| AC Resistance (Ohm) | 6.1 |

Two thermistors were used to monitor the skin and heatsink temperatures. The thermistors were negative temperature coefficient resistors that were surface mounted onto the inside of the ceramic plates on both sides of the thermoelectric module. This allowed for precise control of the applied skin temperature $T_{Skin}$ and monitoring of the heatsink temperature $T_{HS}$ as well as accurate monitoring of the temperature differential across the thermoelectric module $\Delta T_{TEM}$. The devices were positioned on the inside of the subject's forearm during testing.

FIGS. 10A-12B depict plots of heatsink temperature, skin temperature, and the thermal sensations experienced by a user during different methods of cooling down a heatsink from an elevated temperature. Specifically, after a period of active cooling by the wearable thermoelectric system different control methods were implemented to cool the heatsink and the resulting temperatures and thermal sensations experienced by the user were observed.

Figure 10A:
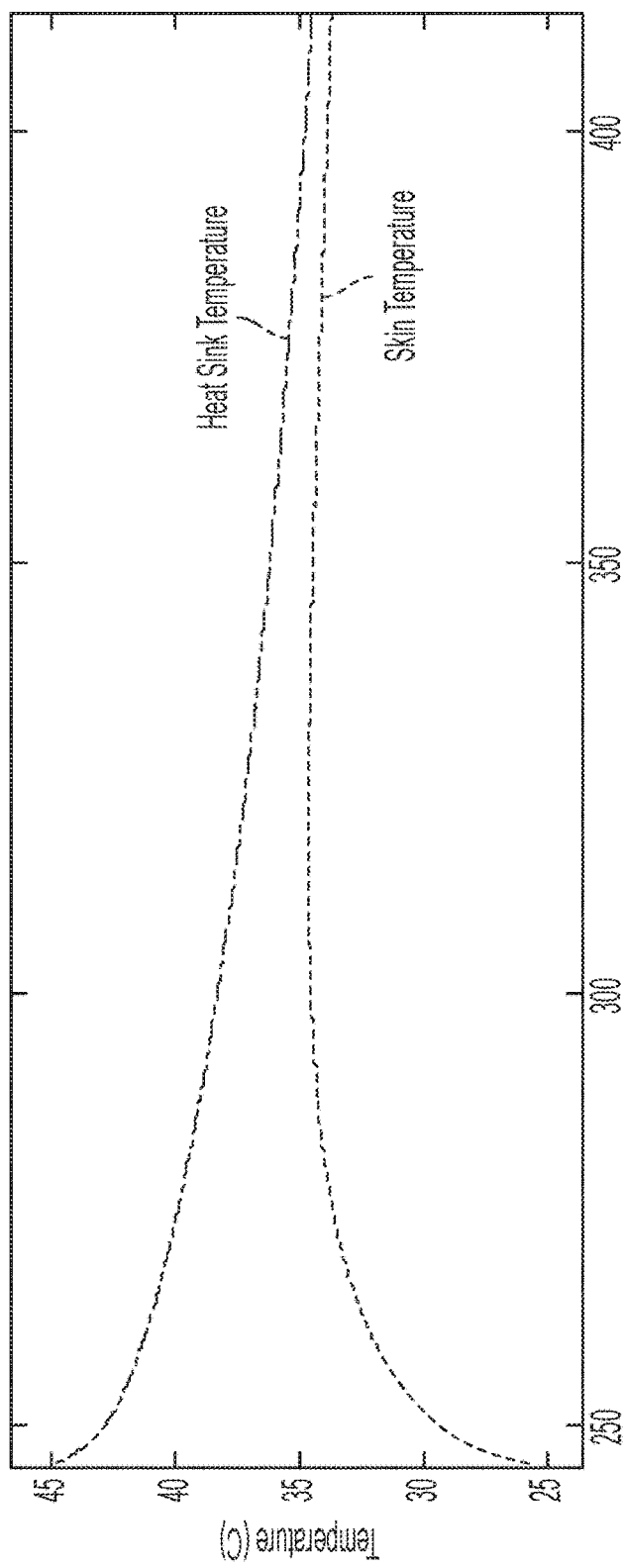
FIG. 10A is a graph of temperature versus time for the skin of a user and a heatsink of a thermal adjustment device after the system has been turned off.
Figure 10B:
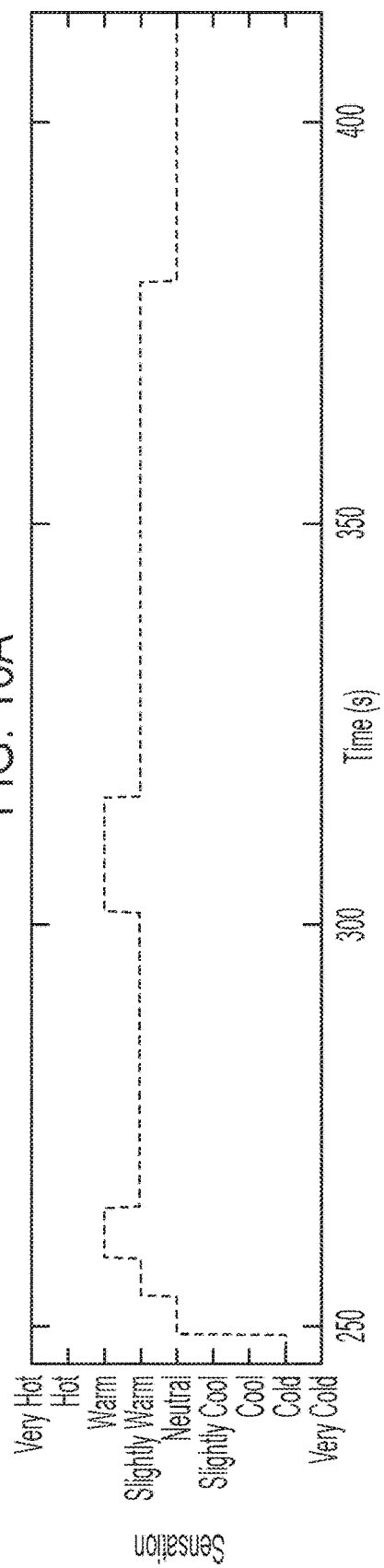
FIG. 10B is a graph of temperature perceptions experienced by a user during the device operation depicted in FIG. 10A.

FIGS. 10A and 10B depict the operation of a system with no control over the temperature applied to the skin of the user during cooling of the heatsink. Prior to shutdown, the applied skin temperature $T_{Sk}$ was initially 25° C. and the heatsink temperature $T_{HS}$ was initially 45° C. To illustrate the problem of continuing to wear a thermoelectric system that has been operated for a period of time, power to the system was shut off without controlling the temperature of the thermoelectric module during thermal equilibration of the system. The sensation plot illustrates noticeable sensations of warmth as the temperature applied to the skin quickly equilibrates to a temperature of out 34° C.-35° C. while the heat sink continues to dissipate heat into both the environment and the user's body.

Figure 11A:
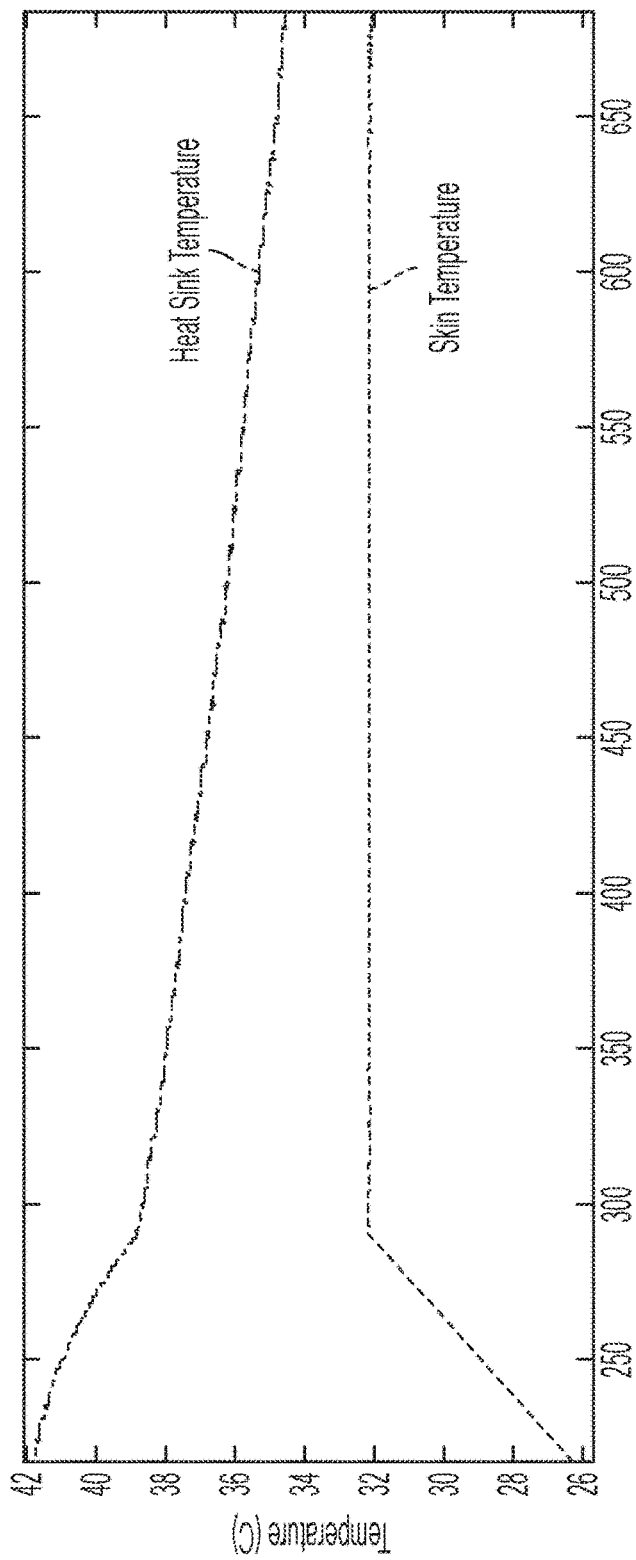
FIG. 11A is a graph of temperature versus time for the skin of a user and a heatsink of a thermal adjustment device during thermal equilibration of the heatsink while maintaining a desired skin temperature.
Figure 11B:
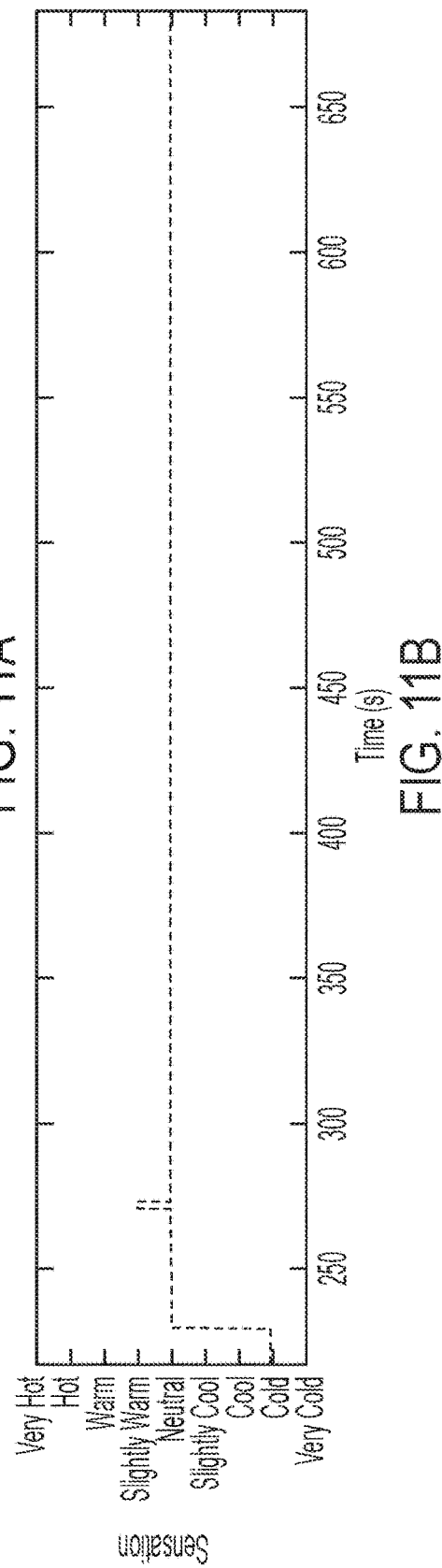
FIG. 11B is a graph of temperature perceptions experienced by a user during the device operation depicted in FIG. 11A.

FIGS. 11A and 11B correspond to a successful cooling of a wearable thermoelectric system that is cooled while controlling the temperature applied to the skin of the user. Specifically, after a period of active cooling the skin temperature $T_{Sk}$ was 26° C. and the heatsink temperature $T_{HS}$ was 42° C. The applied skin temperature was then linearly increased at a rate less than 0.1° C./s to second higher skin temperature of 32° C. As illustrated by the thermal sensation profile, this resulted in the user experiencing a substantially neutral thermal sensation as compared to the warm and hot sensations experienced during cooling of the sink without controlling the skin temperature applied to the user. Additionally, the combination of conditions of the heatsink and applied skin temperature resulted in conditions corresponding to a closed-loop system where the rate of heat dissipation is greater than the thermal load applied to the heatsink (i.e. $Q_{Diss}>Q_{Load}$). Thus, the heatsink temperature $T_{HS}$ continued to decrease throughout the monitored time without generating noticeable sensations of warmth for the user.

Figure 12A:
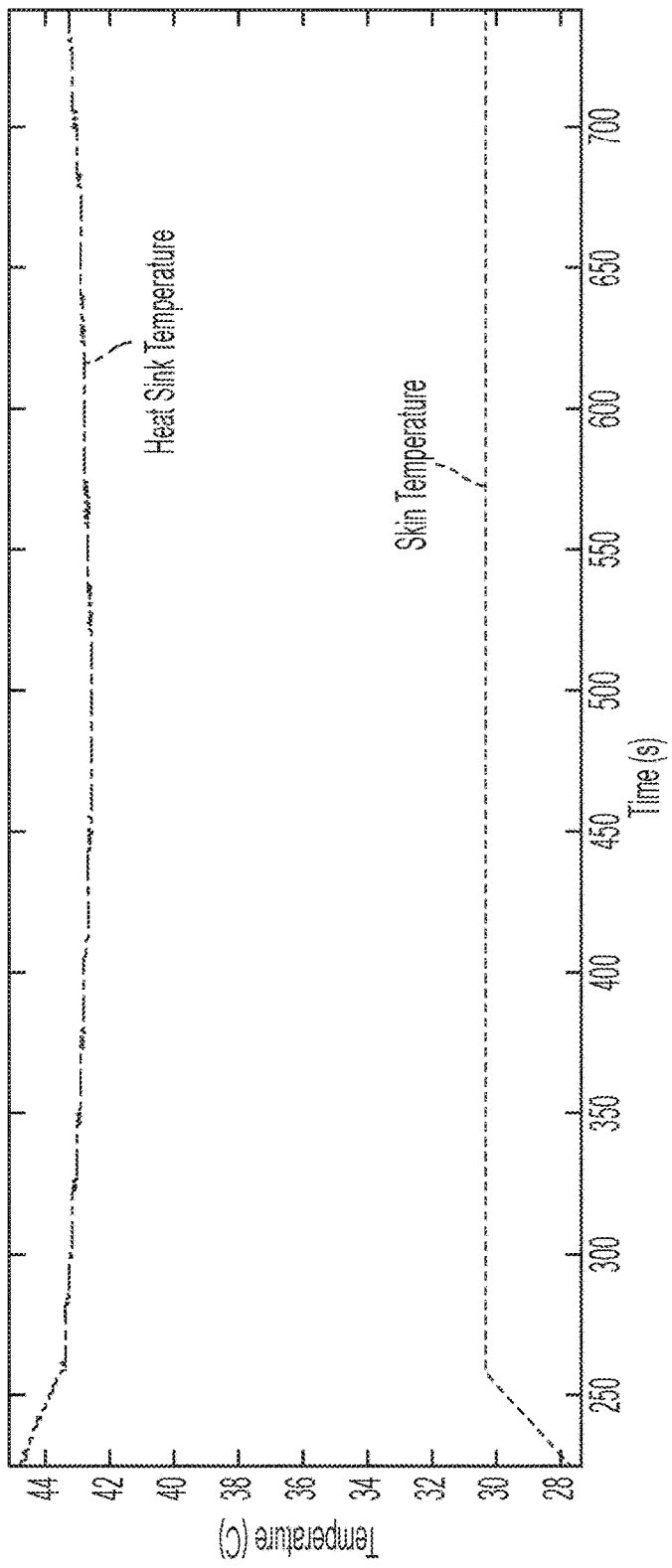
FIG. 12A is a graph of temperature versus time for the skin of a user and a heatsink of a thermal adjustment device where the heatsink is at too high a temperature to permit thermal equilibration of the heatsink to a lower temperature for the applied system temperatures.
Figure 12B:
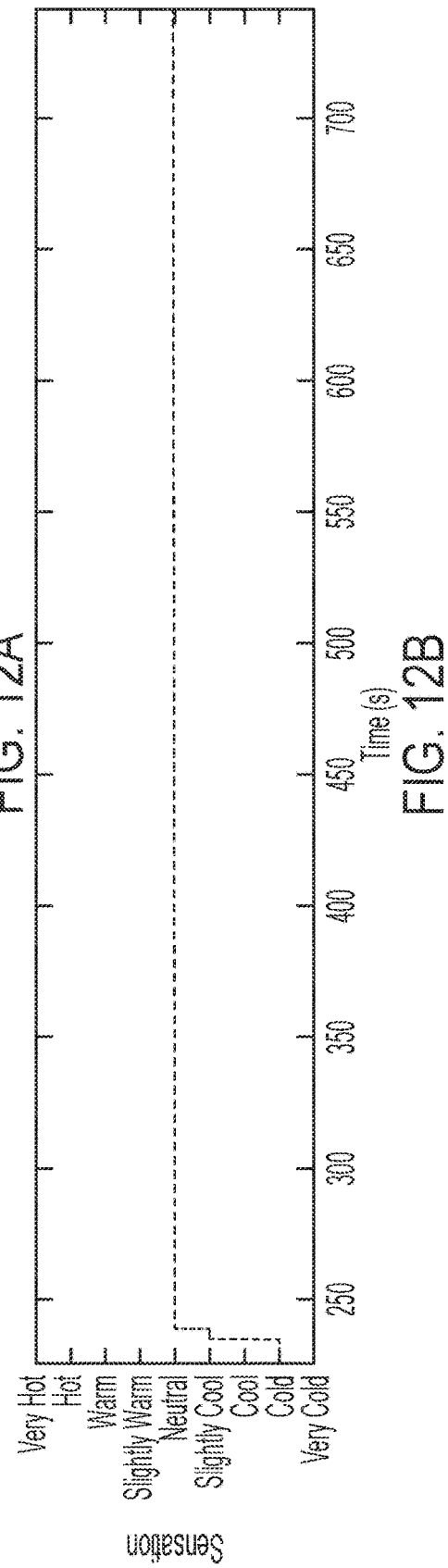
FIG. 12B is a graph of temperature perceptions experienced by a user during the device operation depicted in FIG. 12A.

FIGS. 12A and 12B correspond to an unsuccessful cooling of a wearable thermoelectric system that is cooled while controlling the temperature applied to the skin of the user. Specifically, after a period of active cooling the skin temperature $T_{Sk}$ was 28° C. and the heatsink temperature $T_{HS}$ was 45° C. The temperature was then increased to a skin temperature of 30° C. at a rate that resulted in only neutral thermal sensations being observed by the user. However, in this case the resulting heatsink temperature exceeded the heatsink temperature that permitted appropriate balancing of the rate of heat dissipation by the heatsink and heat generation by the thermoelectric module (i.e. $T_{HS}>T_{HS(Bal)}$). Accordingly, during the temperature equilibration process, the heatsink temperature initially decreased until the rate of heat dissipation by the heatsink was equal to the heat generated by the thermoelectric module (i.e. $Q_{Diss}=Q_{Load}$) for the applied skin temperature. However, the heatsink temperature did not decrease any further. It is expected that if a higher skin temperature were applied, it would have been possible to appropriately cool the heatsink. This confirms the importance of appropriately balancing the rate of dissipation from the heatsink and the rate of heat generation from a thermoelectric module.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single device or distributed among multiple devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a controller or other computing device used to implement the systems and methods described herein may be embodied in any of a number of forms, such as an integrated processor, a rack-mounted computer, a desktop computer, a laptop computer, or a tablet computer. Additionally, a controller or computing device may be embedded in a device not generally regarded as a computing device but with suitable processing capabilities, including a Personal Digital Assistant (PDA), a smart phone or any other suitable portable or fixed electronic device capable of implementing the methods described herein.

Also, a systems described herein may include one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, mice, touch pads, touch screens, gesture recognition modules (e.g. IMU's), and digitizing tablets. As another example, a system may receive input information through speech recognition or in other audible format.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the embodiments described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present disclosure as discussed above. As used herein, the term "computer-readable storage medium" encompasses only a non-transitory computer-readable medium that can be considered to be a manufacture (i.e., article of manufacture) or a machine. Alternatively or additionally, the disclosure may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Some actions are described as taken by a "user." It should be appreciated that a "user" need not be a single individual, and that in some embodiments, actions attributable to a "user" may be performed by a team of individuals and/or an individual in combination with computer-assisted tools or other mechanisms.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for manipulating a temperature of a surface comprising:
   at least one heating and/or cooling element constructed and arranged to be disposed adjacent the surface;
   a heatsink in thermal communication with the at least one heating and/or cooling element and an external environment of the device; and
   at least one controller in electrical communication with the at least one heating and/or cooling element, wherein the at least one controller is configured to:
   cause the at least one heating and/or cooling element to apply a first temperature profile to the surface;
   detect that a temperature of the heatsink has exceeded a first threshold temperature;
   cause the at least one heating and/or cooling element to apply a second temperature profile to the surface upon detecting the temperature of the heatsink has exceeded the first threshold temperature; and
   cause the at least one heating and/or cooling element to apply the first temperature profile to the surface after detecting that the temperature of the heatsink is less than a second threshold temperature that is lower than the first threshold temperature.

2. The device of claim 1, wherein a rate of heat generated by the at least one heating and/or cooling element when the second temperature profile is applied to the surface is less than a rate of heat dissipation from the heatsink.

3. The device of claim 1, wherein the at least one controller is configured to cause the at least one heating and/or cooling element to change the temperature of the surface at a rate between or equal to 0.01° C./s to 1.0° C./s during at least a portion of the first temperature profile.

4. The device of claim 1, wherein a first temperature is applied to the surface during the first temperature profile and a second temperature is applied to the surface during the second temperature profile, and wherein the second temperature is between the first temperature and the temperature of the heatsink.

5. The device of claim 4, wherein the second temperature is between 30° C. and 36° C.

6. The device of claim 4, wherein the second temperature is between an initial temperature of the surface and the temperature of the heatsink.

7. The device of claim 4, wherein the second temperature is between an initial temperature of the surface and the first temperature.

8. The device of claim 4, wherein the at least one controller is configured to cause the at least one heating and/or cooling element to apply the second temperature to the surface after detecting that the temperature of the heatsink has exceeded the first threshold temperature.

9. The device of claim 1, wherein the heatsink is a passive heatsink.

10. The device of claim 1, wherein the at least one controller is configured to cause the at least one heating and/or cooling element to actively cool the surface.

11. The device of claim 1, wherein the at least one heating and/or cooling element is a thermoelectric.

12. The device of claim 4, wherein the at least one controller is configured to cause the at least one heating and/or cooling element to change the first temperature to the second temperature at a first average rate at temperatures below a threshold temperature of the surface and at a second average rate that is less than the first average rate at temperatures above the threshold temperature of the surface.

13. The device of claim 1, wherein the heatsink is configured to dissipate a thermal load during application of the second temperature profile.

14. A method for manipulating a temperature of a surface, the method comprising:
   applying a first temperature profile to the surface;
   detecting a temperature of a heatsink;
   applying a second temperature profile to the surface when the detected temperature of the heatsink exceeds a first threshold temperature;
   dissipating heat from the heatsink while the second temperature profile is applied to the surface; and switching from the first temperature profile to the second temperature profile after a first duration and/or when the temperature of the heatsink is greater than the first threshold temperature, and switching from the second temperature profile to the first temperature profile after a second duration and the temperature of the heatsink is less than a second threshold temperature that is less than the first threshold temperature.

15. The method of claim 14, further comprising maintaining a rate of heat generation less than a rate of heat dissipation from the heatsink when the second temperature profile is applied to the surface.

16. The method of claim 14, wherein a rate of change of the temperature of the surface is between or equal to 0.01° C./s to 1.0° C./s during at least a portion of the first temperature profile.

17. The method of claim 14, wherein a first temperature is applied to the surface during the first temperature profile and a second temperature is applied to the surface during the second temperature profile, and wherein the second temperature is between the first temperature and the temperature of the heatsink.

18. The method of claim 17 wherein the second temperature is between 30° C. and 36° C.

19. The method of claim 17, wherein the second temperature is between an initial temperature of the surface and the temperature of the heatsink.

20. The method of claim 17, wherein the second temperature is between an initial temperature of the surface and the first temperature.

21. The method of claim 14, further comprising detecting that the temperature of the heatsink is less than the second threshold temperature that is lower than the first threshold temperature, and applying the first temperature profile to the surface after detecting that the temperature of the heatsink is less than the second threshold temperature.

22. The method of claim 14, wherein the heatsink is a passive heatsink.

23. The method of claim 17, wherein the first temperature is less than an initial temperature of the surface.

24. The method of claim 14, further comprising applying the first and second temperature profiles to the surface with a thermoelectric.

25. The method of claim 17, wherein the first temperature is changed to the second temperature at a first average rate at temperatures below a threshold temperature of the surface and at a second average rate that is less than the first average rate at temperatures above the threshold temperature of the surface.

26. A method for manipulating a temperature of a surface, the method comprising:
   detecting a temperature of a heatsink;
   selectively applying at least first and second modes of operation to apply thermal stimulation to the surface based on the temperature of the heatsink, wherein:
      the first operating mode includes controlling a temperature of the surface with a first temperature profile; and
      the second operating mode includes controlling the temperature of the surface with a second temperature profile; and
      switching from the first operating mode to the second operating mode after a first duration and/or when a temperature of the heatsink is greater than a first threshold temperature, and switching from the second operating mode to the first operating mode after a second duration and the temperature of the heatsink is less than a second threshold temperature that is less than the first threshold temperature.

27. The method of claim 26, wherein a rate of change of the temperature of the surface is between or equal to 0.01° C./s to 1.0° C./s during at least a portion of the first temperature profile.

28. The method of claim 26, wherein a first temperature is applied to the surface during the first temperature profile and a second temperature is applied to the surface during the second temperature profile, and wherein the second temperature is between the first temperature and the temperature of the heatsink.

29. The method of claim 28, wherein the second temperature is between 30° C. and 36° C.

30. The method of claim 28, wherein the second temperature is between an initial temperature of the surface and the temperature of the heatsink.

31. The method of claim 28, wherein the second temperature is between an initial temperature of the surface and the first temperature.

32. The method of claim 26, further comprising detecting that the temperature of the heatsink has exceeded the first threshold temperature, and switching from the first operating mode to the second operating mode after detecting that the temperature of the heatsink has exceeded the first threshold temperature.

33. The method of claim 32 further comprising detecting that the temperature of the heatsink is less than the second threshold temperature that is lower than the first threshold temperature, and switching from the second operating mode to the first operating mode after detecting that the temperature of the heatsink is less than the second threshold temperature.

34. The method of claim 26, wherein the heatsink is a passive heatsink.

35. The method of claim 28, wherein the first temperature is less than an initial temperature of the surface.

36. The method of claim 26, further comprising applying the first and second temperature profiles to the surface with a thermoelectric.

37. The method of claim 28, wherein the first temperature is changed to the second temperature at a first average rate at temperatures below a threshold temperature of the surface and at a second average rate that is less than the first average rate at temperatures above the threshold temperature of the surface.

38. The method of claim 26, wherein the first operating mode includes applying a first temperature to the surface with the first temperature profile while generating heat at a first rate of heat generation and dissipating heat with the heatsink with a first rate of heat dissipation, wherein the first rate of heat dissipation is less than the first rate of heat generation.

39. The method of claim 38, wherein the second operating mode includes applying a second temperature to the surface with the second temperature profile while generating heat at a second rate of heat generation and dissipating heat with the heatsink with a second rate of heat dissipation, wherein the second rate of heat dissipation is greater than the second rate of heat generation.

40. A device for manipulating a temperature of a surface comprising:
   at least one heating and/or cooling element constructed and arranged to be disposed adjacent to the surface;
   a heatsink in thermal communication with the at least one heating and/or cooling element and an external environment of the device; and at least one controller in electrical communication with the at least one heating and/or cooling element, the at least one controller configured to cause the at least one heating and/or cooling element to selectively apply at least first and second operating modes to apply thermal stimulation to the surface based on a temperature of the heat sink, wherein:

during the first operating mode the at least one controller is configured to cause the at least one heating and/or cooling element to apply a first temperature profile to the surface; and during the second operating mode the at least one controller is configured to cause the at least one heating and/or cooling element to apply a second temperature profile to the surface; and wherein the at least one controller is configured to switch from the first operating mode to the second operating mode after a first duration and/or when a temperature of the heatsink is greater than a first threshold temperature, and wherein the controller is configured to switch from the second operating mode to the first operating mode after a second duration and the temperature of the heatsink is less than a second threshold temperature that is less than the first threshold temperature.

41. The device of claim 40, wherein the at least one controller is configured to change the first temperature profile to the second temperature profile at a rate between or equal to 0.01° C./s to 1.0° C./s.

42. The device of claim 40, wherein a first temperature is applied to the surface during the first temperature profile and a second temperature is applied to the surface during the second temperature profile, and wherein the second temperature is between the first temperature and the temperature of the heatsink.

43. The device of claim 42, wherein the second temperature is between 30° C. and 36° C.

44. The device of claim 42, wherein the second temperature is between an initial temperature of the surface and the temperature of the heatsink.

45. The device of claim 42, wherein the second temperature is between an initial temperature of the surface and the first temperature.

46. The device of claim 40, wherein the at least one controller is configured to apply the second operating mode after detecting that a temperature of the heatsink has exceeded the first threshold temperature.

47. The device of claim 46, wherein the at least one controller is configured to apply the first operating mode after detecting that the temperature of the heatsink is less than the second threshold temperature that is lower than the first threshold temperature.

48. The device of claim 40, wherein the heatsink is a passive heatsink.

49. The device of claim 40, wherein the at least one controller is configured to cause the at least one heating and/or cooling element to actively cool the surface.

50. The device of claim 40, wherein the at least one heating and/or cooling element is a thermoelectric.

51. The device of claim 42, wherein the at least one controller is configured to cause the at least one heating and/or cooling element to change the first temperature to the second temperature at a first average rate at temperatures below a threshold temperature of the surface and at a second average rate that is less than the first average rate at temperatures above the threshold temperature of the surface.

* * * * *